US008921593B2

(12) United States Patent
Kotsianis et al.

(10) Patent No.: US 8,921,593 B2
(45) Date of Patent: *Dec. 30, 2014

(54) PROCESS FOR THE SEMI-CONTINUOUS TRANSVINYLATION OF CARBOXYLIC ACIDS WITH VINYL ACETATE

(75) Inventors: Ilias S. Kotsianis, Houston, TX (US); Barbara F. M. Kimmich, Bernardsville, NJ (US); Melchior A. Meilchen, Houston, TX (US); Hang Wang, Houston, TX (US); Prashant P. Barve, Pune (IN); Bhaskar D. Kulkarni, Pune (IN); Gopal M. Chaphekar, Pune (IN); Ravindra W. Shinde, Pune (IN); Milind Y. Gupte, Pune (IN); Sanjay P. Kamble, Pune (IN); Satish N. Shintre, Pune (IN)

(73) Assignee: Celanese International Corporation, Dallas, TX (US)

( * ) Notice: Subject to any disclaimer, the term of this patent is extended or adjusted under 35 U.S.C. 154(b) by 585 days.

This patent is subject to a terminal disclaimer.

(21) Appl. No.: 13/068,112

(22) Filed: May 3, 2011

(65) Prior Publication Data
US 2011/0275852 A1    Nov. 10, 2011

Related U.S. Application Data

(60) Provisional application No. 61/343,811, filed on May 4, 2010, provisional application No. 61/343,812, filed on May 4, 2010.

(51) Int. Cl.
C07C 67/02 (2006.01)
C07C 53/00 (2006.01)
C07C 67/10 (2006.01)
C07C 51/36 (2006.01)
C07C 51/48 (2006.01)
C07C 51/44 (2006.01)

(52) U.S. Cl.
CPC ............. *C07C 67/10* (2013.01); *C07C 51/36* (2013.01); *C07C 51/48* (2013.01); *C07C 51/44* (2013.01)
USPC ........................................ 560/234; 562/606

(58) Field of Classification Search
USPC ........................................ 560/234; 562/606
See application file for complete search history.

(56) References Cited

U.S. PATENT DOCUMENTS

| 2,245,131 A | 6/1941 | Hermann et al. ............. 260/476 |
| 2,997,494 A | 8/1961 | Brown ....................... 260/410.9 |
| 2,997,495 A * | 8/1961 | Rutledge et al. ............. 554/165 |
| 3,000,918 A | 9/1961 | Wilip et al. ................ 260/410.9 |
| 3,188,319 A | 6/1965 | Smidt et al. .................... 260/326 |
| 3,337,611 A | 8/1967 | Bearden, Jr. et al. ......... 260/491 |
| 3,755,387 A | 8/1973 | Young ..................... 260/410.9 N |
| 4,425,277 A | 1/1984 | Kawamoto et al. .... 260/410.9 N |
| 4,981,973 A | 1/1991 | Murray ........................ 548/229 |
| 5,155,253 A | 10/1992 | Murray ........................ 560/225 |
| 5,210,207 A | 5/1993 | Mokhtarzadeh et al. ...... 548/239 |
| 5,214,172 A | 5/1993 | Waller ......................... 554/165 |
| 5,223,621 A * | 6/1993 | Vallejos et al. ............... 554/165 |
| 5,342,979 A | 8/1994 | Mueller et al. ............... 554/206 |
| 5,741,925 A | 4/1998 | Mao et al. ..................... 560/116 |
| 6,891,052 B1 | 5/2005 | Tanner et al. ................. 554/161 |
| 2011/0275853 A1* | 11/2011 | Kotsianis et al. ............. 560/234 |

FOREIGN PATENT DOCUMENTS

| EP | 1 220 542 | 1/1971 | ............. C07C 51/42 |
| EP | 1 486 443 | 9/1977 | |
| EP | 0 376 075 | 7/1990 | ............. C07C 67/10 |
| EP | 0497340 | * 1/1992 | ............. C07C 67/10 |
| EP | 0 494 016 | 7/1992 | ............. C07C 69/01 |
| EP | 0 497 340 | 8/1992 | ............. C07C 67/10 |
| EP | 0 648 734 | 4/1995 | ............. C07C 67/055 |
| JP | 06-009492 | 1/1994 | ............. C07C 69/24 |
| JP | 07-138203 | 5/1995 | ............. C07C 69/24 |
| JP | 11-171837 | 6/1999 | ............. C07C 69/767 |
| JP | 2002-322125 | 11/2002 | ............. C07C 67/10 |
| JP | 2002-322126 | 11/2002 | ............. C07C 67/10 |

OTHER PUBLICATIONS

Nakagawa et al., "Synthesis of enol and vinyl esters catalyzed by an iridium complex," Tetrahedron Letters, 44, 103-106, 2003.*
Ketterling et al., "Carboxylic acid transvinylation as catalysed by complexes of palladium acetate with phenanthroline-like ligands," Applied Catalysis, 66, 123-132, 1990.*
Armarego et al. Purification of Laboratory Chemicals, 1996 (4th Edition), Elsevier p. 1.*
Slinckx et al., entitled "The Mechanism of Vinyl Interchange by Nuclear Magnetic Resonance Spectroscopy", Tetrahedron, vol. 22, Issue 9 (1966), pp. 3163-3171.
Slinckx et al., entitled "Kinetics of the Vinyl Interchange Reaction Between Benzoic Acid and vinyl Acetate", Tetrahedron, 23 (1967), pp. 1395-1403.
McKeon, et al., entitled "The Palladium (II) Catalyzed Vinyl Interchange Reaction-I", Tetrahedron, vol. 28, pp. 227-232, 1972, Part I.
McKeon, et al., entitled "The Palladium (II) Catalyzed Vinyl Interchange Reaction-", Tetrahedron, vol. 28, pp. 233-238, 1972, Part II.
Ketterling et al., entitled "Carboxylic Acid Transvinylation as Catalysed by Complexes of Palladium Acetate with Phenanthroline-Like Ligands", Applied Catalysis, 66 (1990) pp. 123-132.
Waller, entitled "Transvinylation Catalysts for the Production of Higher Vinylic Esters of Vinyl Acetate", Catalysis of Organic Reactions, Chemical Industries (Dekker) 1994, 53, pp. 397-410.

(Continued)

*Primary Examiner* — Paul A Zucker
*Assistant Examiner* — Mark Luderer
(74) *Attorney, Agent, or Firm* — Michael W. Ferrell; Ferrells, PLLC; Anna L. Kinney

(57) ABSTRACT

A semi-continuous process is provided for selective formation of a vinyl ester by reactive distillation from a corresponding carboxylic acid. Carboxylic acid, vinyl acetate, and a palladium acetate—bidentate ligand catalyst complex are provided and reacted in a typical embodiment. Acetic acid and vinyl acetate are continuously removed from the reaction mixture and vinyl acetate is recycled to the reaction mixture. The vinyl ester product is separated from the vinyl acetate, residual carboxylic acid, residual acetic acid, and catalyst.

14 Claims, 3 Drawing Sheets

(56) References Cited

OTHER PUBLICATIONS

Rashidi-Ranjbar et al., entitled "Synthesis of Aroamtic Vinyl Esters by Exchange Reaction Catalyzed with Pd(II)", Molecules, May 1, 1999 (Iranian Paper), pp. 135-138.

Sabel et al., entitled "Der Durch Salze der Platinmetalle Katalysierte Austausch von Vinyl—Und Anderen Ungesättigten Gruppen Zwischen Estern and Carbonsäuren", Chem. Ber. 102, pp. 2939-2950, 1969.

Murray & Lincoln, entitled "New Catalytic Route to Vinyl Esters", Catalysis Today, 13 (1992) pp. 93-102.

Schultz et al., entitled "The Chemistry of Palladium Complexes VI. Studes on the Palladium(II)-Catalyzed Decomposition of Vinyl Acetate", Journal of Catalysis, 16 (1970) pp. 133-147.

Nakagawa, et al. entitled "Synthesis of Enol and vinyl Esters Catalyzed by an Iridium Complex", Tetrahedron Letters, 44 (2003) pp. 103-106.

T.A. Stephenson, (Mrs.) S.M. Morehouse, A.R.Powell, J.P. Hefter, and Wilkinson, entitled "Carboxylates of Palladium, Platinum, and Rhodium, and Their Adducts", J.C.S., pp. 3632-3640 (1965).

International Search Report and Written Opinion.

* cited by examiner

US 8,921,593 B2

PROCESS FOR THE SEMI-CONTINUOUS TRANSVINYLATION OF CARBOXYLIC ACIDS WITH VINYL ACETATE

CLAIM FOR PRIORITY

This application is based on U.S. Provisional Patent Application No. 61/343,811, entitled Process for the Semi-continuous Transvinylation of Carboxylic Acids with Vinyl Acetate, and U.S. Provisional Patent Application No. 61/343,812, both filed May 4, 2010, the priorities of both which are hereby claimed and the disclosures of which are incorporated herein by reference.

FIELD OF INVENTION

This invention relates to the semi-continuous transvinylation of carboxylic acids with vinyl acetate to vinyl esters by way of homogeneous catalysis.

BACKGROUND OF THE INVENTION

The reaction of carboxylic acids with vinyl acetate monomer (VAM or VA) to make vinyl esters is well known in the literature. The earliest art teaches transvinylation using a mercury catalyst. See U.S. Pat. No. 2,997,494 to Brown, U.S. Pat. No. 3,000,918 to Wilip, et al., and U.S. Pat. No. 3,337,611 to Bearden, Jr., as well as Slinckx et al., Tetrahedron, Volume 22, Issue 9 (1966) Pages 3163-3171 and Slinckx et al., Tetrahedron, 23 (1967) 1395-1403. U.S. Pat. No. 2,245,131 to Herrmann et al. teaches vinyl acetate and benzoic acid transvinylated using a mercury/sulfuric acid catalyst under reflux, and then the volatiles were removed by distillation prior to distillation to recover vinyl benzoate. British Patent No. GB 1486443 to Imperial Chemical describes a transvinylation reaction for the production of a vinyl ester of an organic carboxylic acid by transvinylating a vinyl ester of an organic carboxylic acid with an organic carboxylic acid whose vinyl ester has a lower boiling point than the vinyl ester reactant. Mercury salts are no longer in use due to the toxic nature of mercury-based compounds.

The literature suggests that the preferred catalysts for transvinylation reactions have been mercury- and palladium-based compounds. Transesterification is disclosed by McKeon, et al., Tetrahedron, Vol. 28, p. 227, 1972, Part I. McKeon, et al. show the vinyl interchange reaction between a vinyl ether and an alcohol using a palladium catalyst in a liquid phase batch process. Nitrogen ligands are used to stabilize the catalyst (pyridine). See also McKeon, et al., Tetrahedron, Vol. 28, p. 233, 1972, Part II in which a catalyst precursor is disclosed of either palladium acetate phenyl or palladium acetate biphenyl complexed with monodentate ligands for stability. However, the resulting catalyst was ineffective. Two catalysts prepared were diacetato(2,2'-bipyridyl)palladium(II) and diacetato(1,10-phenanthroline)palladium (II). Vinyl laurate was prepared from lauric acid and vinyl acetate using the palladium acetate complex with 2,2'-bipyridyl. Schultz et al., Journal of Catalysis, 16 (1970) 133-147, discuss the catalyzed decomposition of vinyl acetate into acetic acid and acetaldehyde using a palladium(II)-chloride catalyst. Palladium catalysts are more specifically applied to transvinylation as described in U.S. Pat. No. 3,188,319 to Smidt et al., U.S. Pat. No. 3,755,387 to Young, and U.S. Pat. No. 4,425,277 to Kawamoto et al., as well as Ketterling et al., Applied Catalysis, 66 (1990) 123-132, Waller, Chemical Industries (Dekker) 1994, 53 (Catalysis of Organic Reactions), p 397, Molecules, May 1, 1999 (Iranian Paper), European Patent No. EP376075, and Japanese Patent Nos. JP1994-9492A to Mitsubishi Rayon Co. Ltd., JP1995-138203 to Fuso Chemical Co. Ltd., and JP1999-171837 to Nippon Steel Chemical Co., Ltd. U.S. Pat. No. 3,188,319 to Smidt et al. further discloses use of platinum and rhodium catalysts for less effective transvinylation of various carboxylic acids in a liquid phase with no solvent after forming from a metal chloride or acetate precursor. Ketterling et al. disclose palladium acetate diimine complexes, such as palladium acetate complexes with 2,2'-bipyridine, as catalysts for transvinylation of unsaturated and saturated carboxylic acids. Sabel et al., Chem. Ber. 102, 2939-2950, 1969, describe Pt(II) and Rh(III) used to catalyze a transvinylation reaction. U.S. Pat. No. 4,425,277 to Kawamoto et al. discusses a method for the preparation of alkenyl esters of carboxylic acids, such as benzoic acid, using the combination of a catalyst, such as palladium acetate, and a redox agent. Transvinylation to produce a carboxylic vinyl ester is also taught in Japanese Patent Nos. JP2002-322125 and JP2002-322126 to Japan Vam & Poval Co., Ltd., which describe combining the reactants, palladium acetate catalyst and lithium acetate co-catalyst together and reacting the mixture at 65° C.

Use of ruthenium catalysts in transvinylation is also known in the art. See U.S. Pat. No. 5,155,253 to Murray, as well as Murray & Lincoln, Catalysis Today, 13 (1992) 93-102, which provides a summary of previous patents and Chem Systems Vinyl Neodecanoate (90S8), February 1992, which provides a review of ruthenium transvinylation as well as addressing palladium catalyzed transvinylation. U.S. Pat. No. 4,981,973 to Murray discloses that ruthenium compositions are useful transvinylation catalysts for numerous Bronsted acids and derivatives of Bronsted acids. However, the Murray processes require a carbon monoxide atmosphere, which requires careful handling.

Iridium catalysis, with a NaOAc additive, of liquid phase batch transvinylation of benzoic and other acids with a substituted alkyne is described by Nakagawa, et al. in Tetrahedron Letters 44 (2003) 103-106. The iridium catalyst is formed from a $[Ir(cod)Cl]_2$ precursor.

U.S. Pat. No. 5,210,207 to Mokhtarzadeh, et al. teaches continuous transvinylation by reactive distillation. Mokhtarzadeh, et al. discloses a process for the preparation of numerous vinyl derivatives of Bronsted acids formed by the transvinylation reaction of a vinyl derivative of a first Bronsted acid and a second Bronsted acid wherein the vinyl product ester is less volatile than the vinyl reactant ester. In particular, Mokhtarzadeh, et al. teaches reacting vinyl acetate and benzoic acid to produce vinyl benzoate or reacting vinyl acetate with 2-ethylhexanoic acid to produce vinyl 2-ethylhexanoate. See, particularly, Examples 4 and 8. Mokhtarzadeh, et al. further provides for removal of the reaction product from the column to avoid reflux and thus aid the reactive distillation process; reactants are recycled to the reactor. Ruthenium catalyst concentrations of from about 30,000 ppm to about 0.01 ppm based on the weight of the liquid phase reaction medium and reaction temperatures of from about 20° C. to about 300° C. are disclosed, with a ruthenium concentration of 50-75 ppm and a temperature of 125-135° C. disclosed in Examples 4 and 8, and a temperature of 140-145° C. disclosed in Example 3. However, the Mokhtarzadeh process achieves poor yields.

U.S. Pat. No. 6,891,052 to Tanner et al. teaches formation of a vinyl ester using a zinc carboxylate catalyst and acetylene gas. Tanner et al. teaches batch operation at a temperature of about 205° C. See Examples 1 and 2, which exemplify synthesis of vinyl neodecanoate.

European Patent No. 0648734 A1 to Packett discloses synthesis of higher vinyl esters directly from ethylene in the presence of palladium cupric salt catalysts, but achieves very low yield. See Examples 2-11, 22, 26-27, 29-32, 36-39 and 41-43, wherein vinyl 2-ethylhexanoate is prepared at yields of up to 69%; Example 12 which discloses production of vinyl butyrate; Examples 18, 25 and 34, wherein synthesis of vinyl neodecanoate is disclosed in yields up to 37%; Examples 19 and 35, wherein synthesis of vinyl benzoate in yields of 21% is disclosed; Examples 20-21, in which synthesis of a mixture of vinyl adipate compounds having a combined yield of up to 46% is disclosed.

U.S. Pat. No. 5,223,621 and EP 0 494 016 B1 to Vallejos et al. teach transvinylation of carboxylic acids, including benzoic acid, with VAM in the presence of a catalyst and ligand in a system that incorporates reflux. Vallejos et al. disclose a palladium acetate (II)—2,2'-bipyridyl complex catalyst formed in situ in a mole ratio of 2,2'-bipyridyl to palladium (II) acetate of about 3:1. See particularly Examples 6 and 8. In example 8, Vallejos et al. describes using 8721 ppm of palladium equivalent per kg of benzoic acid and a VAM to acid ratio of 5:1. After a reaction time of 6 hours, the process according to Vallejos et al. achieved a yield of 89%. The transvinylation reaction disclosed by Vallejos et al. provides a TON of 0.12 kg VB/g Pd. However, the combined use of palladium (II) acetate and 2,2'-bipyridyl is only described in Example 6. The catalyst recovery taught by Vallejos et al. involves precipitation and filtration of palladium from the reaction medium, after which the product is removed by distillation. The temperature of the reaction is held at or below 100° C. to maintain catalyst stability.

U.S. Pat. No. 5,214,172 to Waller discloses catalytic transvinylation of a carboxylic acid to form a vinyl ester. Waller further teaches reactants including vinyl acetate and aliphatic and aromatic mono-carboxylic acids reacted in the presence of a palladium catalyst introduced to the reaction mixture as palladium acetate complexed with an aryl N-containing ligand, such as 2,2'dipyridyl or 1,10-phenanthroline. However, Waller only provided working examples for transvinylation of stearic acid and dicarboxylic acids including suberic, adipic, glutaric, and succinic acids, and found the catalyst complexes having 2,2'-dipyridyl or 1,10-phenanthroline ineffective for use with dicarboxylic acids.

U.S. Pat. No. 5,741,925 to Mao et al. teaches transvinylation of naphthenic acids, which are classified as monobasic carboxylic acids of the formula $C_nH_{2n-z}O_2$, where n indicates the carbon number and z is zero for saturated acyclic acids and 2 for monocyclic acids, for example, with a vinyl ester, such as vinyl acetate. The process of Mao et al. is directed primarily to $C_{10}$ to $C_{20}$ carboxylic acids, as evidenced by claims 2 and 8. Catalysts used in the transvinylation process of Mao et al. include palladium acetate complexed with one or more aryl N-containing ligands, such as 1,10-phenanthroline or 2,2'-dipyridyl. Mao et al. further teaches that the catalysts can be recycled over several uses.

From the foregoing, it is clear that the existing processes utilize toxic catalysts such as mercury catalysts and/or are not appropriate for economically viable industrial scale operations. Furthermore, there is an unmet need for economically viable catalysts that produces vinyl esters with high selectivity, high conversion and in short reaction campaign times from the reaction of VAM and other carboxylic acids in a semi-continuous operation.

SUMMARY OF THE INVENTION

The new semi-continuous transvinylation process described in the present invention will result in a more economical route to vinyl ester monomers compared to conventional batch reaction setups.

There is thus provided in a first aspect of the invention a semi-continuous process for selective formation of a vinyl ester from its corresponding carboxylic acid. In the formation process, a carboxylic acid and vinyl acetate are fed to a reactor and reacted in the presence of a homogeneous transvinylation catalyst in a reaction mixture to form a vinyl ester product and acetic acid. Acetic acid and vinyl acetate are preferably continuously removed from the reaction mixture and at least a portion of the vinyl acetate is separated from the acetic acid and recycled to the reaction mixture. The reaction mixture may be periodically withdrawn as a crude vinyl ester product mixture and a purified vinyl ester product may be separated from residual carboxylic acid, residual vinyl acetate, residual acetic acid, and homogeneous transvinylation catalyst.

The process according to the invention is generally characterized in various embodiments by a conversion of carboxylic acid to vinyl ester product with a selectivity of at least 80 mole %, and a crude product mixture containing less than 15 weight % acetic acid. These characteristics may be achieved by selection of catalyst and carboxylic acid reactant and by controlling the esterification reaction conditions, feed to the reaction mixture, removal of acetic acid from the reaction mixture, and the separation and recycling of vinyl acetate to the reaction mixture.

Other aspects and advantages of the present invention are described in the detailed description below and in the claims.

BRIEF DESCRIPTION OF THE DRAWINGS

The invention is described in detail below with reference to the appended drawings, wherein like numerals designate similar parts. In the Figures.

DETAILED DESCRIPTION OF THE INVENTION

Figure 1:
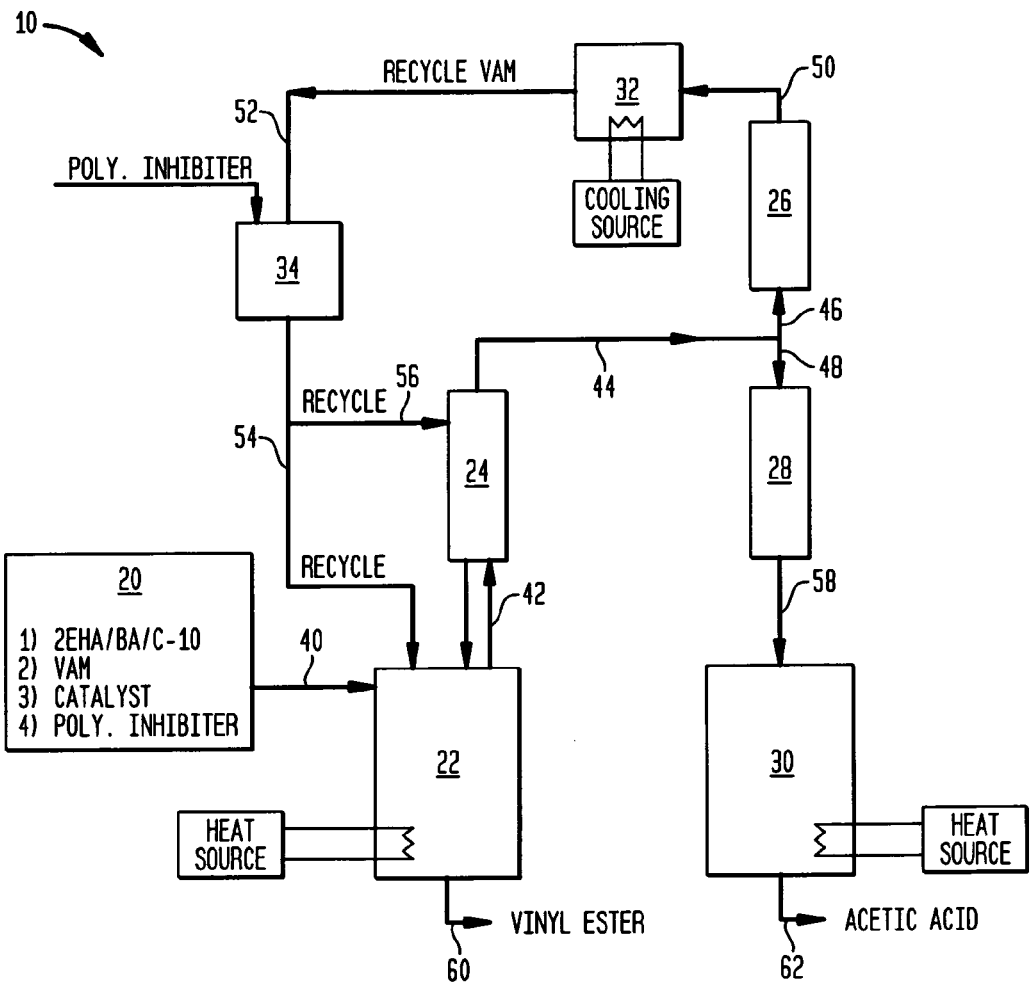
FIG. 1 is a process flow diagram illustrating a semi-continuous apparatus suitable for the production of vinyl esters.

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below.

Percent, % and so forth refers to mole percent, unless the usage or context clearly indicates otherwise.

The transitional phrase "consisting essentially of" limits the scope of a claim to the specified materials or steps "and those that do not materially affect the basic and novel characteristic(s)" of the claimed invention. As used herein with respect to process claims, "consisting essentially of" means that the steps are carried out in the recited sequence and exclude steps therebetween that involve substantial reaction of an intermediate or final product; for example, intermediate steps would not involve reaction of more than about 10% of the intermediate product. With respect to product claims, "consisting essentially of" and like terminology refers to the recited components and excludes other ingredients which would substantially change the basic and novel characteristics of the composition or article. Unless otherwise indicated or readily apparent, a composition or article consists essentially of the recited components when the composition or article includes 90% or more by weight of the recited components. That is, the terminology excludes more than 10% unrecited components.

"Platinum group metal" means and includes iridium, osmium, palladium, platinum, rhodium and ruthenium.

As used herein, the reference to palladium content is differentiated from catalyst or catalyst complex content in that palladium content refers to the weight or mole fraction of the catalyst or catalyst complex that is palladium metal atoms.

"Selectivity" refers to the amount of vinyl ester produced relative to the carboxylic acid consumed and is expressed as a mole percent based on converted carboxylic acid. Selectivity to vinyl ester (VE) is calculated from gas chromatography (GC) data using the following equation:

$$\text{Selectivity to } VE(\%) = 100 * \frac{\text{mole } VE, \text{ out } (GC)}{\text{mole } CA, \text{ in} - \text{mole } CA, \text{ out } (GC)}$$

Where mole CA, in=mole of carboxylic acid loaded into the reactor, mole CA, out (GC)=mole of carboxylic acid after the reaction based on GC data, and mole VE, out (GC)=mole of vinyl ester after the reaction based on GC data.

"Conversion" refers to the fraction of reactant consumed in the reaction and is expressed as a mass percentage based on the initial carboxylic acid (reactant) in the feed. The conversion of carboxylic acid (CA) is calculated from gas chromatography (GC) data using the following equation:

$$CA \text{ conversion}(\%) = 100 * \frac{\text{mass } CA_{feed} - \text{mass } CA, \text{ out } (GC)}{\text{mass } CA_{feed}}$$

Where mass $CA_{feed}$=mass of carboxylic acid loaded (weighed in) into the reactor, and mass CA, out (GC)=mass of carboxylic acid after the reaction based on GC data.

"Yield" refers to the amount of carboxylic acid converted to vinyl ester formed and may be determined using the following equation:

$$\text{Yield}(\%) = \frac{\text{selectivity} \times \text{conversion}}{100}$$

where selectivity and conversion are determined as disclosed above. Alternatively, yield may be determined by dividing the moles of ester formed by the moles of carboxylic acid fed, multiplied by 100.

The catalyst activity may be determined herein by turn over number (TON) using the following equation:

$$\text{TON} = \frac{\text{kg product formed over one or more production cycles}}{\text{g of Pd from the initial charge}}$$

TON generally refers to the average amount of desired product produced by each metal atom contained in the catalyst while the catalyst charge remains active. The term "g of Pd" refers to the initial palladium mass charged to the reactor which is recycled back to the reactor for each production cycles. TON may also be calculated as kg product formed per g of palladium charged over a specified number of production cycles. As used herein, initial TON for a semi-continuous reactor refers to the product formed for one fresh and two recycle runs per g of palladium initially charged, unless otherwise indicated.

Hourly Catalytic Productivity as used herein refers to the rate of formation of the product as a function of the amount of catalyst used and is analogous to a space time yield. Hourly Catalytic Productivity is reported in kg vinyl ester per hour per gm catalyst metal and is calculated as follows:

$$\text{Hourly Catalytic Productivity} = \frac{\text{TON, kg/g}}{\text{Total reaction time, hr}}$$

Where the total reaction time is the sum of the reaction times for all of the campaigns or cycles for which the TON was calculated. For purposes of this application, the total reaction time was calculated for eight 16-hour campaigns, resulting in a total reaction time of 128 hours.

As used herein, the term "reaction mixture" refers to the liquid mass in the reactor that contains reagents, catalyst, and optionally solvent.

Various carboxylic acids known in the art can be employed in the process of this invention to form corresponding vinyl esters. The acids that are suitable in this invention may include, but not necessarily be limited to, the following acids:

2-ethylhexanoic acid, benzoic acid, neodecanoic acid, propionic acid, butyric acid, valeric acid, heptanoic acid, acrylic acid, methacrylic acid, stearic acid, and palmitic acid Preferably, the vinyl esters produced in the process of this invention include vinyl 2-ethylhexanoate (V2EH), vinyl benzoate (VB), vinyl neodecanoate (NAVE-10), vinyl propionate, vinyl butyrate, vinyl valerate, vinyl heptanoate, vinyl acrylate, vinyl methacrylate, vinyl stearate, and vinyl palmitate.

The transvinylation process can alternatively be practiced with a carboxylic acid and a vinyl ester other than vinyl acetate as raw materials, or with a carboxylic acid and mixtures of vinyl esters. Suitable vinyl esters include all of the above-mentioned vinyl esters as well as the homologous series of each above-mentioned vinyl ester and fatty acid esters, for example vinyl laurate.

Neodecanoic acid is a member of the neo acid family. Neo acids are highly branched aliphatic carboxylic acids. In general, neo acids are trialkyl acetic acids, which include a tetra substituted alpha-carbon. Alkyl groups on the substituted alpha-carbon create a steric effect, i.e. hinder the ability of the neo acid to react. Methyl substituted alpha-carbon neo acids are the least hindered of the neo-acids. The reactivity of the neo acid primarily depends on the molecular weight and structure of the neo acid. In general, the greater the molecular weight of the alkyl groups on the alpha-carbon, the greater the steric effect and the less reactive the neo acid. Neodecanoic acid in particular is a mix of isomers of $C_{10}H_{20}O_2$ having an average molecular weight of approximately 172 grams/mole. Two examples of such isomers are shown below.

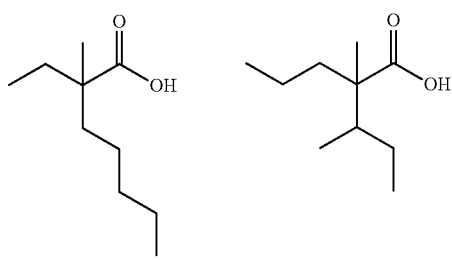

A vinyl ester of the present invention is derived from a neodecanoic acid that has the following general structure:

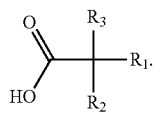

Formula I where $R_1$ and $R_2$ are alkyl groups which together may typically collectively contain about 7 carbon atoms, that is, on average, and $R_3$ is generally a methyl group. Vinyl neodecanoate refers to a vinyl ester of a saturated, branched monocarboxylic acid having an average of 10 carbon atoms in the acid radical.

The process according to the invention comprises reactive distillation at reflux temperature as a semi-continuous process. A carboxylic acid, such as 2-ethyl hexanoic acid (2-EHA), benzoic acid (BA) or neodecanoic acid (C-10); vinyl acetate; and a palladium acetate (II)—2,2'-bipyridyl catalyst complex are charged to a reactor. Byproduct acetic acid formed during the reaction is continuously removed from the reactor as a vapor along with vinyl acetate vapor. The byproduct vapor is routed through a fractionation assembly to recover excess vinyl acetate, which is recycled back to the reactor. Excess vinyl acetate is recovered by distillation at atmospheric pressure or mild vacuum (e.g., about 500 to 760 mm Hg). Byproduct acetic acid is subsequently recovered by vacuum distillation. Finally, product vinyl ester is recovered under reduced pressure. Catalyst and unconverted carboxylic acid remain, with a very small amount of product, providing at a minimum 15 catalyst recycles per reaction time. Vinyl ester recovered from this process is generally at least 95% pure. Trace amounts of acetic acid may remain. This process achieves higher productivity. The transvinylation reactions are generally described by the representative chemical formulas shown below.

Catalyst Preparation. Several catalysts may be used for transvinylation, as disclosed by McKeon et al., Tetrahedron, Vol. 28, pp. 227-238, 1972. These catalysts may include simple Pd(II) salts of strong acids such as $PdCl_2$, and Pd(II) salts of weak acids, such as Pd(II) acetate, complexed with monodentate or bidentate ligands, such as pyridine, triethylphosphine, triphenylphosphine, 2,2'-bipyridyl, and 1,10-phenanthroline. Cis palladium acetate complexes have shown to be particularly stable, and bidentate ligands have shown to be more effective than monodentate ligands. Some examples of effective catalysts include diacetato(2,2'-bipyridyl)palladium(II), diacetato(1,10-phenanthroline)palladium(II), diacetato-(N,N,N',N'-tetramethylethylenediamine)palladium(II) and diacetato(P,P,P',P'-tetraphenyl-1,2-diphosphinoethane)palladium(II). The catalyst is prepared separately from the reactive distillation process using standard procedure as reported in JCS (T. A. Stephenson, (Mrs.) S. M. Morehouse, A. R. Powell, J. P. Heffer, and Wilkinson, J. C. S., 3632-3640 (1965)).

Continuous removal of acetic acid from the reaction zone. Acetic acid is removed continuously out of the reaction zone with the help of VAM to shift the equilibrium of Formula II or Formula III, above, to the right. A binary mixture of acetic acid and VAM reduces the temperature at which acetic acid vaporizes, allowing acetic acid removal at a temperature below the deactivation temperature of the catalyst used in the invention. More than about 90 wt % to 95 wt % of the acetic acid formed is removed from the reaction zone.

VAM recycling and use of lower VAM concentrations. VAM is distilled out and supplied back to the reaction zone allowing use of a lower molar ratio of VAM/reactant carboxylic acid than is disclosed in the prior art. With the process according to the invention, the amount of VAM required approaches a theoretical ratio based on stoichiometry and thus reduces or eliminates the need for excess VAM in the

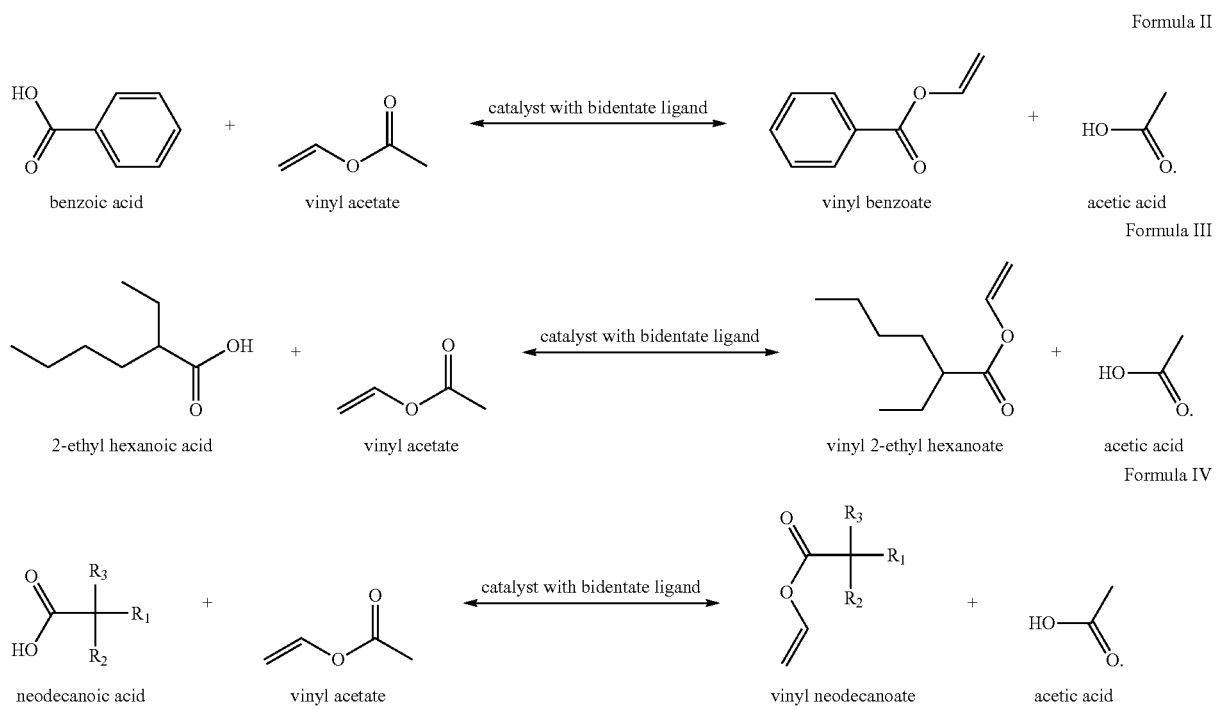

reaction zone. The molar ratio of VAM to carboxylic acid in the reaction zone ranges from at least 1:1 up to less than 9:1.

Conversion rates. Generally, a minimum of 75 wt % of the carboxylic acid charged is converted to vinyl ester per pass. Product selectivity is more than 99 mol %, based on the carboxylic acid charged to the reaction. The turnover number (TON) achieved was at least 20 kg of vinyl ester per gram of palladium without deactivation of the catalyst.

Reactor designs. A conventional continuous stirred-tank reactor (CSTR) in combination with a number of distillation columns may be employed in the process according to the invention. In particular, use of a small distillation column coupled to a CSTR provides for minimal VAM reflux, reducing vinyl ester loss into the acetic acid stream. Therefore, such a design improves process economics.

Reflux ratios and flow rates. The process according to the invention allows the use of minimized reflux ratios in the reaction zone columns. VAM recovered from the process is 99.9% pure and can be immediately reused in the reaction. VAM recycle ratios range from about 0.5:1 to about 7:1.

Catalyst concentration. An amount of catalyst providing about 150 ppm to about 2325 ppm equivalent palladium is provided based on the mass of carboxylic acid reactant. Preferably, the concentration of catalyst metal is from 250 ppm to 2000 ppm, and in some embodiments, from 500 to 1000 ppm of palladium. Palladium (Pd) concentrations below 250 ppm Pd were achieved while maintaining conversion values above 70 wt %, for example, concentrations as low as about 130 ppm Pd were achieved. Ruthenium (Ru) on an active carbon support may alternatively be used as a heterogeneous catalyst.

Reaction conditions. Reaction temperatures of a process according to the invention are lower than conventional processes. The reaction is performed at atmospheric pressure. The reaction temperature may range from about 80° C. to about 120° C. Preferably the temperature of the reaction is maintained from about 90° C. to about 110° C. However, low catalyst concentrations require higher reaction temperatures. The molar ratio of vinyl acetate to the reactant carboxylic acid charged to the reactor is about 2.2:1 to about 9:1. Ratios may be less than about 4:1, and ratios of less than 2:1 have been achieved in some cases. The reaction time ranges from less than about 3 hours to about 36 hours depending upon the catalyst concentration and acetic acid removal rate.

Continuous inhibitor addition. An inhibitor is added to the reaction and to the crude and purified products to prevent vinyl ester polymerization. Without inhibitor addition, side reactions may occur resulting in homopolymers or copolymers of the vinyl ester reactant and/or product. Such reactions impact quality and yield and have adverse safety implications. Any suitable inhibitor may used, such as hydroquinone (HQ), methoxy hydroquinone (MeHQ), butylated hydroxytoluene (BHT), tert-butyl catechol (TBC), or phenothiazine.

Coproduction of acetic acid-VAM mix. This process produces a mixture rich in acetic acid. This mixture is drawn off from the process and may be utilized directly or with minimal processing in VAM plants. Alternatively, acetic acid may be separated from the mix. Byproduct acetic acid may be used as a reactant in subsequent processes. Experiments using the Pd catalyst complex of the invention resulted in VAM:acetic acid molar ratios ranging from 0.5:1 to 14.4:1 in the recovered mixture. Preferably, the vinyl acetate:acetic acid molar ratio removed from the reaction mixture is from about 1.5:1 to about 10:1 or about 1:1 to about 9:1. More preferably, the process results in a molar ratio of VAM:acetic acid of from about 2:1 to about 7:1; and even more preferably, the process results in a molar ratio of VAM:acetic acid 2.5:1 to 6:1.

Small Distillation column on top of the Transvinylation Reactor. Minimization of VAM reflux reduces the loss of the produced ester (VB, V-2-EH, or NAVE-10) into the acetic acid rich stream. Incorporation of a small distillation column allows such minimization and thus improves process economics.

Purification of carboxylic acid reagent. Surprisingly, in some cases, carboxylic acid reagents demonstrating otherwise high levels of purity have been found to contain impurities that cause deactivation of the catalyst during transvinylation. These impurities may include compounds having alcohol functional groups; compounds having ester functional groups; compounds having olefinic functional groups; compounds having peroxide functional groups; sulfur; and other electropositive metals. It has been further surprisingly discovered that a number of purification methods may be effective in reducing these impurities. These methods may include flash distillation; fractionation; extraction, e.g., water wash (i.e., multistage extraction with water); hydrogenation; and combinations thereof. Preferably, the purification method includes at least extraction, wherein the carboxylic acid is repeatedly water washed for from about ½ hour to about 2 hours and subject to phase separation. In some embodiments, the purification method is hydrogenation followed by water wash. The catalyst selected for hydrogenation remains active for at least 50 cycles of hydrogenation, and may be palladium on a carbon support. The purified carboxylic acid may be distinguished from impure, or crude, carboxylic acid in that it is characterized by a bromine value of less than 20 mmoles of $Br_2/g$, preferably 18 mmoles of $Br_2/g$ or less, and still more preferably less than 10 mmoles of $Br_2/g$; a peroxide value of less than 200 ppm, preferably less than 100 ppm, and still more preferably less than 20 ppm; or a permanganate time of more than 30 minutes, preferably more than 60 minutes and most preferably more than 120 minutes.

EXAMPLES

Examples 1 & 2

Scale-Up Study & Pilot Runs for V-2-EH & VB

The catalyst life and recycle number information generated in lab scale experiments, discussed in further detail below, was used to design an experiment to test catalyst life, to identify a highest achievable turn over number (TON), and to study product purification and isolation. The scale-up was carried out using a semi-continuous reaction approach.

Description of Apparatus

Transvinylation was performed using a semi-continuous apparatus of the class shown in FIG. 1. The reaction system 10 mainly comprised a feed vessel 20; a stirred reactor 22 provided with a small packed column 24; a second packed column, comprising an upper rectification section 26 and a lower stripping section 28, configured to receive vaporized components from the reactor 22; a stirred reboiler 30; a condenser 32; and a distillate receiver 34. The temperatures of the reactor 22, distillation column 26, 28, reboiler 30 and condenser 32 were controlled by conventional means known in the art. Flowrates to the reactor 22 and small column 24 were also controlled by conventional means.

The feed vessel 20 contained pre-mixed feed to be charged to the reactor 22 through line 40. Pure VAM was charged continuously to the top of the column 24 via line 56. Distilled VAM recovered in distillate receiver 34 was continuously fed via line 54 to the reactor 22, which helped to maintain the reaction temperature. Vapors leaving the reactor 22 passed to the first column 24 via line 42. Vapors leaving the first column 24 via the vapor take off line 44 entered the middle of the second rectification column between the upper rectification section 26 and the lower stripping section 28. Components of the vapors passing upward through the rectification section 26 are indicated by line 46, and components of the vapors passing downward through the stripping section are indicated by line 48. From the rectification section 26, the lighter components exited via line 50, were condensed in condenser 32, and collected via line 52 in receiver 34. The heavier components exited the stripping section 28 of the distillation column via line 58 and were collected in the reboiler 30. The contents of the reactor 22 and the reboiler 30 were removed at the end of the cycle at 60 and 62, respectively.

Experimental Procedure

The entire assembly was flushed with nitrogen. The catalyst complex for the 2-EHA experiments was divided into two equal portions; one portion to be charged to the reactor 22, and the other portion to be charged to the feed vessel 20. The carboxylic acid, vinyl acetate, catalyst complex (half of the catalyst complex for the 2-EHA runs), and hydroquinone were initially charged to the reactor 22. Similarly, vinyl acetate and hydroquinone were initially charged to the reboiler 30. A mixture of vinyl acetate and 2,2'-bipyridyl; and for the V-2EH runs, 2-ethylhexanoic acid, catalyst complex, and hydroquinone; was prepared and stored in the feed vessel 20.

The reaction mass in the reactor 22 and the contents of the reboiler 30 were heated to the boiling point of vinyl acetate. The reaction mass in the reactor 22 was further heated until VAM started distilling out through the vapor take off line 44. The vapor mixture of VAM and acetic acid emitting out of the first column 24 entered the second column 26, 28 over the reboiler 30. The reboiler 30 was maintained under total reflux condition until the vapor mixture from the reactor 22 reached the distillation column 26, 28, at which time the reflux was altered to and maintained at 0.6 values and the distilled VAM was collected in the distillate receiver 34.

As soon as the reactor 22 temperature reached 78 to 80° C., VAM feed was started to the first column 24.

The reaction temperature of the reactor 22 rose slowly from 72° C. to 100° C. over a period of around 45 minutes. As soon as the reaction temperature reached 98° C., distilled VAM was fed to the reactor 22 via line 54. The rate was adjusted to maintain the reaction temperature at 100 to 101° C. The reaction continued at this temperature till the desired conversion of CA was achieved.

Then the feed vessel 20, fed pre-mixed feed to the reactor 22, at a rate of about half of the recycle rate of distilled VAM, until all the feed was consumed. The feed vessel 20 was then rinsed with a small amount of VAM from the distillate receiver 34. The total feed time was up to about 11 to 12 hours. During this time the reaction temperature was maintained at 100 to 101° C.

The reaction continued till desired conversion of CA was obtained at 100 to 101° C. with continuous distillation and recycling of VAM at a desired rate.

After the reaction, the contents of the reboiler 30, and then the contents of the reactor 22, were cooled. The contents of the reactor 22, reboiler 30, and distillate receiver 34 were removed and weighed.

Processing of Reaction Mixture

The reaction mixture was charged to a rotary evaporator (not shown) of a class known to one of skill in the art. Initially, evaporator conditions were 300 mbar vacuum and a temperature of 75° C. VAM and acetic acid were allowed to distill out and were collected. When the rate of distillation decreased, the vacuum was reduced to 100 mbar and the temperature increased to 85° C. The distillate was collected. The distillate contained VAM, acetic acid and a small amount of vinyl ester product. For vinyl benzoate, at this point, the hot reaction mass was transferred to a stirred, jacketed crystallizer (not shown) of a class known in the art.

For vinyl 2-ethylhexanoate, distillation further slowed, and the pressure was reduced to 10 mbar and the temperature increased to 90° C. V-2-EH was allowed to distill and was separately collected. This distillate mainly contained V-2-EH and a small amount of acetic acid and 2-EHA, and is herein identified as crude V-2-EH.

When distillation ceased, the contents were cooled and the vacuum released. The residue was preserved for recycle. This residue contained mainly 2-EHA, a small amount of V-2-EH and the catalyst.

Crystallization of Un-Reacted BA

The reaction mass transferred from the rotary evaporator was cooled in the crystallizer and held for several hours. The slurry was removed and filtered over a vacuum filter. The solid, semi-dried cake of BA was weighed, and the solid cake of BA was preserved for recycle in the next cycle. The mother liquor was weighed and transferred to a conventional evaporator (not shown) for recovery of VB.

Recovery of VB

From 8 to 10 mbar of vacuum was applied. The temperature was raised to 85 to 97° C. VB was allowed to distill out and was separately collected. The distillate mainly contained VB and a small amount of acetic acid and BA. This is identified herein as crude VB. Recovery continued until solid BA started appearing in the distillation still at which stage recovery ceased.

When distillation stopped, the contents were cooled and the vacuum released. The residue of unreacted BA & catalyst was preserved for recycle. This residue contained mainly BA, a small amount of VB and the catalyst.

Purification of Crude Vinyl Ester

The crude V-2-EH or VB was charged to a conventional fractional distillation column (not shown) under vacuum. Around 50 ppm of HQ was added as a stabilizer. Vacuum was applied up to about 50 to 60 mbar, and the crude mass was heated. Distillation started at around 65 to 70° C. The distillate was collected with reflux set to 1. This distillate contained VAM and acetic acid and was recycled to the reactor 22.

The pressure was increased to 8 to 10 mbar as the temperature reached 80 to 85° C., the temperature at which V-2-EH starts distilling, or as the temperature reached 94 to 95° C., the temperature at which VB starts distilling, respectively. After removing a small initial cut (fore cut), the main pure vinyl ester cut was collected. The fore cut was recycled in the next purification. The heavy ends from purification were removed and preserved for recycle in the next reaction cycle. The pure cut was more than 99.6% pure with respect to V-2-EH, and more than 99.8% pure with respect to VB, and demonstrated low acid values (less than 1) and APHA values (less than 15), among other quality tests.

Methoxy hydroquinone (MeHQ) was added to a weighed amount of pure vinyl ester at a concentration of 30 mg per kg of vinyl ester. It was well-mixed and stored in a cool, dry place. Alternative inhibitors may include hydroquinone (HQ), butylated hydroxytoluene (BHT), tert-butyl catechol (TBC), diphenylamine, phenothiazine, or a hindered phenol, for example NALCO™ polymerization inhibitor.

Processing of Reboiler Mixture

Pre-weighed reboiler 30 contents and VAM & acetic acid cuts collected as described above were charged to a conventional fractional distillation unit (not shown). A vacuum of up to 525 mbar was applied. The contents were heated to boiling (60° C.), at which point VAM started distilling out. The system was initially kept under total reflux. When the temperature stabilized at 55° C., VAM collection began under reflux (60:40 ratio). The VAM collection continued until the temperature reached 70° C. Keeping the system under total reflux, pressure was slowly reduced to 300 mbar and the system was allowed to stabilize. Then VAM collection continued under reflux. The distilled VAM was stabilized by adding 30 ppm of HQ. This recovered VAM was recycled in the next reaction cycle.

Once the VAM cut was over, the vacuum was reduced to 325 mbar, allowing acetic acid to distill and collect under reflux.

Analysis of the reaction mixture determined that the acetic acid content was below 12 wt % in the production of vinyl benzoate, and less than 10 wt % in the production of vinyl 2-ethyl hexanoate.

The results obtained for V-2-EH and VB using a Diacetato palladium(II), 2,2'-bipyridyl catalyst are shown in Table 1. As noted in the discussion for Table 5, below, additional cycles increase the TON achieved by the process described herein. TONs of greater than 20 kg vinyl ester/g Pd were achieved by performing additional recycle runs with the catalyst of this experiment. The activity of the catalyst was confirmed by testing a portion of the catalyst separated from the vinyl ester product. The catalyst was combined with a known amount of carboxylic acid and vinyl acetate and maintained at reaction conditions in an autoclave for three hours. A conversion of greater than 30 wt % verified continuing catalyst activity.

TABLE 1

Vinyl ester production reaction performance.

| | Example 1: Vinyl 2-ethylhexanoate production | Example 2: Vinyl benzoate production |
|---|---|---|
| Size of pilot batch | 6 kg | 3 kg |
| Conversion of carboxylic acid, wt % | 80.73% | 76.83% |
| Catalyst amount used, Palladium mg | 801.34 | 559.41 |
| Catalyst complex used, mg | 2864.94 | 2000.00 |
| Pd concentration, ppm | 131.54 | 183.78 |
| Moles of carboxylic acid input | 42.31 | 24.95 |
| Amount of product formed, gm mol | 34.16 | 19.17 |
| Reaction time (Initial charge heating + Feeding mixture + Time required to achieve conversion), hr | 39.75 | 41 |
| VAM recycle rate to transvinylation reactor, L/h | 0.5 | 0.8 |
| Average product formation rate, gm mol of vinyl ester/1 gm of Palladium-per hr | 1.07 | 0.84 |
| Turn Over Number (TON) of catalyst at the end of one fresh & two recycle runs, kg of vinyl ester/1 gm of Palladium | 21.7 | 15.2 |
| Hourly Catalytic Productivity, kg vinyl ester/gm Palladium/hr | 0.182 | 0.125 |
| Rate of formation of product kg/l-h | 0.017 | 0.012 |
| Productivity of vinyl ester, kg of vinyl ester/Liter | 0.68 | 0.48 |

Note:
The catalyst was active after recycle.

Selectivity toward vinyl ester product formation in both transvinylation reactions was close to 100%. No impurities were detected in analysis by gas chromatography (GC) and gas chromatography—mass spectroscopy (GC-MS) techniques.

Product Purification and Product Specifications:

The crude product isolated in both pilot plant runs were 95% pure. The remaining 5% was either 2-EHA or BA with some traces of acetic acid. The crude product was subjected to fractional distillation under reduced pressure. The pressure and temperature were set to 10 millibar and 80° C. with a reflux ratio of 1:2. The fractionation procedure was guided by GC analysis. Product of desired quality was isolated in both cases. The products V-2-EH and VB were stabilized by incorporating 30 ppm of MeHQ. Note that the boiling point for V-2-EH is 185.3° C., compared to the 228° C. boiling point of 2-EHA. Products having the following specifications were isolated.

TABLE 2

Analysis of Vinyl Ester Product from Pilot Plant Runs.

| Analytical parameter | Example 1: Vinyl 2-ethyl hexanoate Observed value | Example 2: Vinyl Benzoate Observed value |
|---|---|---|
| Density | 0.86 gm/cc @ 30° C. | 1.06 gm/cc @ 30° C. |
| Acid value | 0.52 mg of KOH/gm of sample | 0.074 mg of KOH/gm of sample |
| Purity by GC | 99.68% | 99.88% |
| APHA Value | 3.3 | 15.6 |
| MS Spectra | Complies | Complies |
| NMR | Complies | Complies |

During product purification, both products were isolated with very low acid numbers. Thus, aqueous processing of product to remove acidity was avoided.

Example 3

Catalyst Preparation

Catalyst was prepared using palladium acetate and a bidentate ligand such as 2,2'-bipyridyl. This catalyst was prepared generally using toluene as the solvent. Palladium (II) acetate was heated in toluene to 80° C. A solution of 2,2'-bipyridyl in toluene was added over a one hour period. The reaction was continued for two to four hours and then the catalyst reaction mixture was cooled. A catalyst complex, having a mole ratio of palladium (II) acetate to 2,2'-bipyridyl of from about 1:1.1 to 1:1.4, precipitated as a solid. The precipitate was filtered, washed with toluene, and dried under reduced pressure prior to use.

Another catalyst was prepared using a different bidentate ligand such as 1,10-Phenanthroline. The solubility of 1,10-Phenanthroline is negligible in toluene even at high temperature. Hence instead of toluene, acetonitrile, a very polar solvent, was used for preparation of the catalyst complex. Alternative solvents that may be used for preparation of a catalyst according to the invention include toluene, acetonitrile, xylene, benzene, hexane, and cyclohexane. The performance of this catalyst was compared with the catalyst prepared by using 2,2'-bipyridyl as the bidentate ligand.

Another set of catalysts were prepared using monodentate ligands such as either pyridine, to prepare a diacetato palladium (II)-bis-pyridyl complex, or quinoline, to prepare a diacetato palladium (II)-bis-quinolinyl complex. In both cases toluene was used as the solvent. When pyridine was used as the monodentate ligand, the catalyst could not be isolated in powder form, so it was used in solution with toluene. The quinoline-containing catalyst was successfully isolated. The catalyst complexes were tested and compared with the use of bipyridyl complex.

The palladium content for each experiment, expressed in ppm, based on the mass of carboxylic acid charged, was calculated according to the following equation.

$$Pd\ concentration = \frac{[catalyst\ weight,\ md] \times [ratio\ of\ Pd\ MW\ to\ Complex\ MW]}{[weight\ of\ carboxylic\ acid,\ kg]},$$

Examples 4-7

Effect on Transvinylation Reaction Using Catalyst Prepared with Bi-Dentate Ligand A catalyst was prepared by using 1,10-phenanthroline as bi-dentate ligand. The catalyst prepared was a diacetato-palladium (II)-1,10-phenanthroline complex. The catalyst was isolated in solid form, dried and used in the reaction.

A V-2-EH run was performed with a palladium concentration of 626 ppm based on the mass of 2-EHA in a batch system. After six hours running at 100° C., the conversion achieved was 84.26%. A VB run was also performed with a palladium concentration of 626 ppm based on the mass of BA in a batch system. After six hours running at 100° C., the conversion achieved was 75.56 wt %. In both runs, vinyl acetate was provided in a molar vinyl acetate:carboxylic acid ratio of 4:1. The catalyst performance for each run was at par with the catalyst prepared by using a bi-dentate bipyridyl ligand.

TABLE 3

Ligand effect on transvinylation.

| | Example No. | | | |
|---|---|---|---|---|
| | 4 | 5 | 6 | 7 |
| Ligand | Bis-pyridyl complex | Bis-pyridyl complex | 1,10-phenanthroline | 1,10-phenanthroline |
| Carboxylic Acid | BA | 2-EHA | BA | 2-EHA |
| Reaction volume, Liters | 2.01 | 1.83 | 2.01 | 1.83 |
| Pd concentration, ppm | 1230 | 1193 | 626 | 626 |
| Maximum conversion of CA, wt % | 49.98 | 23.35 | 75.56 | 84.26 |
| Time required to attain max. conversion, hr | 9.3 | 7 | 6 | 6 |
| Moles of product formed in above time, gm mol | 2.05 | 0.81 | 3.1 | 2.93 |
| Product formation rate, gm mol/gm Pd per hr | 0.36 | 3.64 | 1.65 | 1.56 |
| Product formation rate, kg/liter reactor volume-hr | 0.016 | 0.011 | 0.038 | 0.045 |

Note:
Bis-quinolinyl complex is not represented in the above table because the reaction was unsuccessful.

Examples 8 & 9

Study of Transvinylation Reaction Using 5% Ru/Activated Carbon

The reaction was studied in a semi-continuous mode using 2-EHA as a substrate. The temperature was maintained at 135° C. Ru/activated carbon was added in a concentration of 500 ppm Ru based on the mass of 2-EHA. VAM was provided in a molar ratio of VAM:2-EHA of 2:1. Hydroquinone was provided in the reactor at a concentration of 459 ppm.

An apparatus of the class shown in FIG. 1 was used for Example 8, where the reactor (1) was 3-liter capacity and reboiler (5) was of 2-liter capacity. Initially, the entire assembly was flushed with nitrogen. The materials, including 2-EHA (2160 gm) & catalyst (61 gm) (Ru/activated carbon) along with HQ (1 gm), were weighed and charged to the reactor and feed vessel. Stirring and heating of the reaction mixture was started. The reaction temperature increased to 130° C. over a period of around 3 hours, at which point VAM was charged to the reactor at a rate of 2.3 ml/min. Distilled VAM was recycled continuously to the reactor, maintaining reaction mass temperature at around 125 to 130° C. After 8 hours, only 5 wt % conversion of 2-EHA to V-2-EH was observed.

Similarly, the reaction was studied in a batch mode in Example 9, where a VAM & 2-EHA mixture (4 moles to 1 mole) was heated in the presence of 500 ppm Ru/carbon based on the mass of 2-EHA. The reaction volume was 3.16 liters. The procedure was the same as described for batch mode reactions above. After 8 hours of reaction, 47.48 wt % conversion of 2-EHA to V-2-EH was observed. In that time, 2.85 moles of V-2-EH formed, giving a reactor productivity of 0.15 kg V-2-EH/liter reactor volume.

Examples 10-13

Comparative Example: Study of Transvinylation in a Batch Mode Reaction Using Redox System

Example 10

Diacetato Palladium (II)-2,2'-Bipyridyl+Cu(Ac)$_2$+Potassium Bromide System

A run was carried out in batch mode using VAM and 2-EHA in 4:1 mole ratio at around 65 to 67° C. in the presence of the above-mentioned catalyst system for 24.5 hours. The palladium concentration used was 500 ppm of Palladium based on the mass of 2-EHA. Even after 24 hours of reaction, noticeable conversion of 2-EHA was not observed. The reaction mixture does not dissolve highly polar potassium bromide.

Example 11

Pd Acetate+CuCl$_2$+Potassium Acetate System

A run was carried out in batch mode using VAM and 2-EHA in 4:1 mole ratio at around 65 to 67° C. in the presence of the above-mentioned catalyst system for 22 hours. The palladium concentration used was 500 ppm of Palladium based on the mass of 2-EHA. The maximum conversion achieved was 41.92% of 2-EHA. The reaction mixture does not dissolve highly polar potassium acetate.

Example 12

Pd Acetate+Cu(Ac)$_2$+Potassium Bromide System

A run was carried out in batch mode using VAM and 2-EHA in 4:1 mole ratio at around 65 to 67° C. in the presence of the above-mentioned catalyst system for 24 hours. The palladium concentration used was 500 ppm of Palladium based on the mass of 2-EHA. The maximum conversion achieved was 14.75 wt % of 2-EHA. The reaction mixture does not dissolve highly polar potassium bromide.

Example 13

PdCl$_2$+FeCl$_3$+Magnesium Carbonate System

A run was carried out in batch mode using VAM and 2-EHA in 4:1 mole ratio at around 65 to 67° C. in the presence of the above-mentioned catalyst system for 22 hours. The palladium concentration used was 500 ppm of Palladium based on the mass of 2-EHA. The maximum conversion achieved was 43.88 wt % of 2-EHA. The reaction mixture does not dissolve magnesium carbonate.

TABLE 4

Transvinylation using Redox systems.

| | Example No. | | | |
|---|---|---|---|---|
| | 10 | 11 | 12 | 13 |
| Catalyst | PdAc-biP—CuAc-Potassium bromide | PdAc—CuCl$_2$-Potassium acetate | PdAc—CuAc-Potassium bromide | PdCl$_2$—FeCl$_3$-Magnesium carbonate |
| Pd complex conc., ppm | 1787.59 | 1055 | 1054.51 | 834 |
| Maximum conversion of 2-EHA, wt % | 0.00 | 41.92 | 14.75 | 43.88 |
| Time required to attain max. conversion, hr | 24.4 | 22 | 24.5 | 22 |
| Moles of product formed in above time, gm mol | 0 | 1.46 | 0 | 1.52 |
| Product rate of formation, gm mol/gm Pd per hr | 0 | 0.07 | 0 | 0.07 |
| Reactor Productivity, kg product/liter reactor volume | 0 | 0.13 | 0 | 0.14 |

Examples 14-21

Catalyst Recycle Runs

The catalyst complex (diacetato-palladium (II)-2,2'-bipyridyl) for preparation of V-2-EH in reactive distillation (semi-continuous setup) was recovered with the vinyl ester product and the catalyst was recycled for seven times after recovery. The palladium concentration used per lot of 2-EHA (432 gm 2-EHA per pass) was 2325 ppm based on the mass of 2-EHA. Vinyl acetate was provided in a molar ratio of VAM:2-EHA of 6.2:1. The time required for 75 wt % conversion was less than three hours. As shown in Table 5, below, turnover number (TON) steadily increases with additional cycles and the catalyst remains active.

Examples 22-35

Effect of Impurities on Catalyst Recycle

The same catalyst complex (diacetato-palladium (II)-2,2'-bipyridyl) for preparation of vinyl neodecanoate (NAVE-10) in reactive distillation (semi-continuous setup) was recovered with the vinyl ester product and the catalyst was recycled for ten times after recovery. The C-10 feed was not purified prior to reaction. The palladium concentration used per lot of neodecanoic acid (C-10 acid; 200 gm per pass) was maintained at 750 ppm based on the mass of C-10 acid. Distilled vinyl acetate was provided in a molar ratio of VAM:C-10 acid of 6:1. The reaction step was operated in a 5 L autoclave for 10 hours at 100° C. The reaction mixture was cooled, weighed, and sampled for GC analysis. The vinyl ester was then recovered using a rotary evaporator. The residue was recycled for the next reaction cycle. The reaction mixture was replenished with enough C-10 acid to maintain the same amount for each pass, and the catalyst was replenished with 10 ppm for each pass. As shown in Table 6, below, the catalyst deactivated quickly.

TABLE 6

Effect of C-10 acid impurities on semi-continuous transvinylation to vinyl neodecanoate.

| | Example No. | | |
|---|---|---|---|
| | 22 | 23 | 24 |
| Type of run | Fresh | 1$^{st}$ recycle | 2$^{nd}$ recycle |
| % Yield of NAVE-10 | 80.86 | 75.44 | 22.13 |

The process described for Examples 22-24 was repeated, except that the neodecanoic acid was purified prior to reaction. As shown in Table 7, below, turnover number (TON) steadily increased with additional cycles and the catalyst remained active. Conversion remained stable with subsequent cycles. The highest concentration of acetic acid measured in the product was 6.91 wt % in the tenth recycle.

TABLE 5

Effect of catalyst recycling on reactive distillation transvinylation using 2-EHA to V-2-EH.

| | Example No. | | | | | | | |
|---|---|---|---|---|---|---|---|---|
| | 14 | 15 | 16 | 17 | 18 | 19 | 20 | 21 |
| Type of run | Fresh catalyst | First recycle | Second recycle | Third recycle | Fourth recycle | Fifth recycle | Sixth recycle | Seventh recycle |
| Moles of 2-EHA | 3.0 | 3.0 | 3.0 | 3.0 | 2.75 | 2.65 | 2.41 | 2.08 |
| Catalyst | Note-1 | Note-2 | Note-2 | Note-2 | Note-2 | Note-2 | Note-2 | Note-2 |
| Palladium conc., ppm | 2325 | 2325 | 2325 | 2325 | 1517 | 1574 | 1724 | 2006 |
| Reaction temperature | 87 to 88° C. | 87 to 88° C. | 92 to 94° C. | 92 to 94° C. | 92 to 94° C. | 92 to 94° C. | 92 to 94° C. | 92 to 94° C. |
| Final conversion of 2-EHA | 76.29% | 70.24% | 70.04% | 79.76% | 74.61% | 70.6% | 70.06% | 69.93% |
| Time in hrs. | 3.0 | 3.0 | 3.5 | 3.0 | 4.5 | 4.5 | 3.5 | 3.0 |
| TON, kg V-2-EH/g Pd | 0.389 | 0.747 | 1.104 | 1.5107 | 1.8905 | 2.42 | 2.898 | 3.310 |

Note-1-
Catalyst used was Diacetato Palladium (II) -2,2'-bipyridyl complex. Fresh charge.
Note-2-
The catalyst was recovered in the earlier run and recycled in the subsequent runs.

TABLE 7

Effect of catalyst recycling on reactive distillation transvinylation using pretreated C-10 acid to vinyl neodecanoate.

| | Example No. | | | | | |
|---|---|---|---|---|---|---|
| | 25 | 26 | 27 | 28 | 29 | 30 |
| Type of run | Fresh catalyst | First recycle | Second recycle | Third recycle | Fourth recycle | Fifth recycle |
| Moles of C-10 Acid | 1.2 | 1.2 | 1.2 | 1.2 | 1.2 | 1.2 |
| Final formation of NAVE-10 | 75.23% | 74.48% | 74.50% | 74.62% | 73.83% | 73.84% |
| TON, kg NAVE-10/g Pd | 0.24 | 0.48 | 0.72 | 0.96 | 1.20 | 1.43 |

| | Example No. | | | | |
|---|---|---|---|---|---|
| | 31 | 32 | 33 | 34 | 35 |
| Type of run | Sixth recycle | Seventh recycle | Eighth recycle | Ninth recycle | Tenth recycle |
| Moles of C-10 Acid | 1.2 | 1.2 | 1.2 | 1.2 | 1.2 |
| Final formation of NAVE-10 | 73.27% | 72.83% | 72.39% | 71.76% | 71.44% |
| TON, kg NAVE-10/g Pd | 1.67 | 1.90 | 2.14 | 2.37 | 2.60 |

Examples 36-42:

Neodecanoic Acid Purification

Generally, C-10 acid is available at 99.5-99.9% purity. However, it was discovered that in some cases impurities in the raw carboxylic acid were poisoning the catalyst in successive cycles. These impurities are believed to include dimers, trimers, di-hydric/polyhydric alcohols and esters of nonene formed during production of C-10 acid, as well as impurities introduced with raw materials in the production of C-10 acid. In order to remedy the situation, a process to purify neodecanoic acid by azeotropic distillation and a catalytic hydrogenation process were developed.

Without intending to be bound by any particular theory, it is believed catalyst poisoning occurs by way of a variety of impurities, including olefinic impurities including alkene impurities, alcohol impurities, ester impurities, sulfur and other electropositive metals, oxidizable impurities generally including unsaturated compounds and aldehydes, for example.

Various purification methods are described below and summarized in Table 8. Note that unpurified (crude) C-10 acid is presented as Example 36 for comparison.

The characteristics determined for the purified acids included bromine value and peroxide value. The determination of bromine value is essential for determination of double bond components present in the C-10 acid, while the peroxide value is also necessary to predict catalyst stability. Solutions are prepared and standardized for both procedures as described in steps I) and II) below. The analytical procedures for determining both bromine value and peroxide value are also provided below.

I) Preparation of Solutions
The following solutions are prepared according to procedures known in the art:
A 0.1N solution of sodium thiosulfate.
A 1% Starch Solution in boiled distilled water.
A 10% KI solution in distilled water (10 gms KI in 100 ml water)

II) Standardization: Normality of Thiosulfate Solution
0.05 g $K_2Cr_2O_7$ is dissolved in 50 ml distilled water to which 5 ml concentrated HCl are added. In a conical flask, the potassium chromate solution is added to 20 ml 10% KI solution, and titrated with the 0.1 N sodium thiosulfate solution until a dark reddish color changes to a faint pale color. One to three drops of starch indicator is then added to the flask and titration is continued until the color changes to a faint green fluorescent color. Three such readings are recorded.

Procedure for Determination of Bromine Value
In addition to the solutions prepared as described above, a mixed solution of potassium bromate and potassium bromide comprising about 2.7 gm of $KBrO_3$ and 17.5 gm of KBr in 1000 ml of distilled water is also prepared.

III) Blank Titration
50 ml of water and 25 ml of the potassium bromated/potassium bromide mixture are mixed with 5 ml of concentrated HCl. After 20 minutes in a dark room, 20 ml of 10% KI are added. The mixture is titrated against the 0.1N sodium thiosulfate solution until a dark reddish-brown color changes to a faint reddish-brown color. Then one drop of starch indicator is added, and the solution becomes a dark bluish color. Titration with sodium thiosulfate continues until the solution becomes colorless. This is the end point of the titration.

IV) Sample Titration
In a 250 ml conical flask, 0.1 gm of sample is dissolved in 10 ml of methanol. To this solution, 50 ml of water, 25 ml of $KBr/KBrO_3$ mixture and 5 ml of concentrated HCl is added. After 20 min in a dark room, 20 ml of 10% KI is added. The solution is titrated with sodium thiosulfate until a dark reddish-brown color changes to a faint reddish brown color. Then one drop of starch indicator is added, and the solution becomes a dark bluish color. Titration with sodium thiosulfate continues until the solution becomes colorless. This is the end point of the titration.

Procedure for Determination of Peroxide Value
III) Blank Titration
In a conical flask, 20 ml of water, 50 ml of MeOH and 5 ml of concentrated HCl are combined with 20 ml of 10% KI and 2 to 3 drops of starch indicator. The solution is titrated with the 0.1 N sodium thiosulfate solution until a pale yellow color becomes colorless. This is the end point of the titration.

IV) Sample Titration
In a 250 ml conical flask, 4 to 5 gm of sample are dissolved in 50 ml of methanol and combined with 20 ml of water, 5 ml of concentrated HCl, 20 ml of 10% KI and 2 to 3 drops of starch indicator. The resultant solution is titrated with the 0.1 N sodium thiosulfate solution until a pale yellow color solution becomes colorless. This is the end point of the titration.

Permanganate Time
Permanganate times are an indication of oxidizable impurities in the feed such as unsaturated compounds, aldehydes and so forth that reduce potassium permanganate. Unless otherwise indicated, permanganate times are measured in accordance with ASTM Test Method D1363-06 at 15° C. with an observation interval of 30 minutes.

(1) Example 37

Flash Distillation (i.e., Flashing)

In the azeotropic distillation purification process, raw neodecanoic acid mixed with a glycol entrainer is fed to a first distillation column. The entrainer forms a hetero-azeotrope with impurities in the raw acid. The hetero-azeotrope of entrainer and impurities is withdrawn from the top of the first distillation column. The impurities are separated from the entrainer by phase separation, and the entrainer is recycled to the first column. Partially purified neodecanoic acid is withdrawn from the bottom of the first distillation column and fed to a second distillation column. Most of the remaining impurities are withdrawn from the top of the second column. The near-pure neodecanoic acid is then fed to a third distillation column for polishing. Purified neodecanoic acid, having a purity of 99.5 to 99.99%, is withdrawn from the top of the third column. Heavy impurities are removed from the bottom of the third column. Note that the permanganate test was negative, indicating that no easily oxidized groups remained. This result was present for all of the purification methods discussed herein.

(2) Example 38

Multistage Extraction with Water (i.e., Water Wash)

Figure 2:
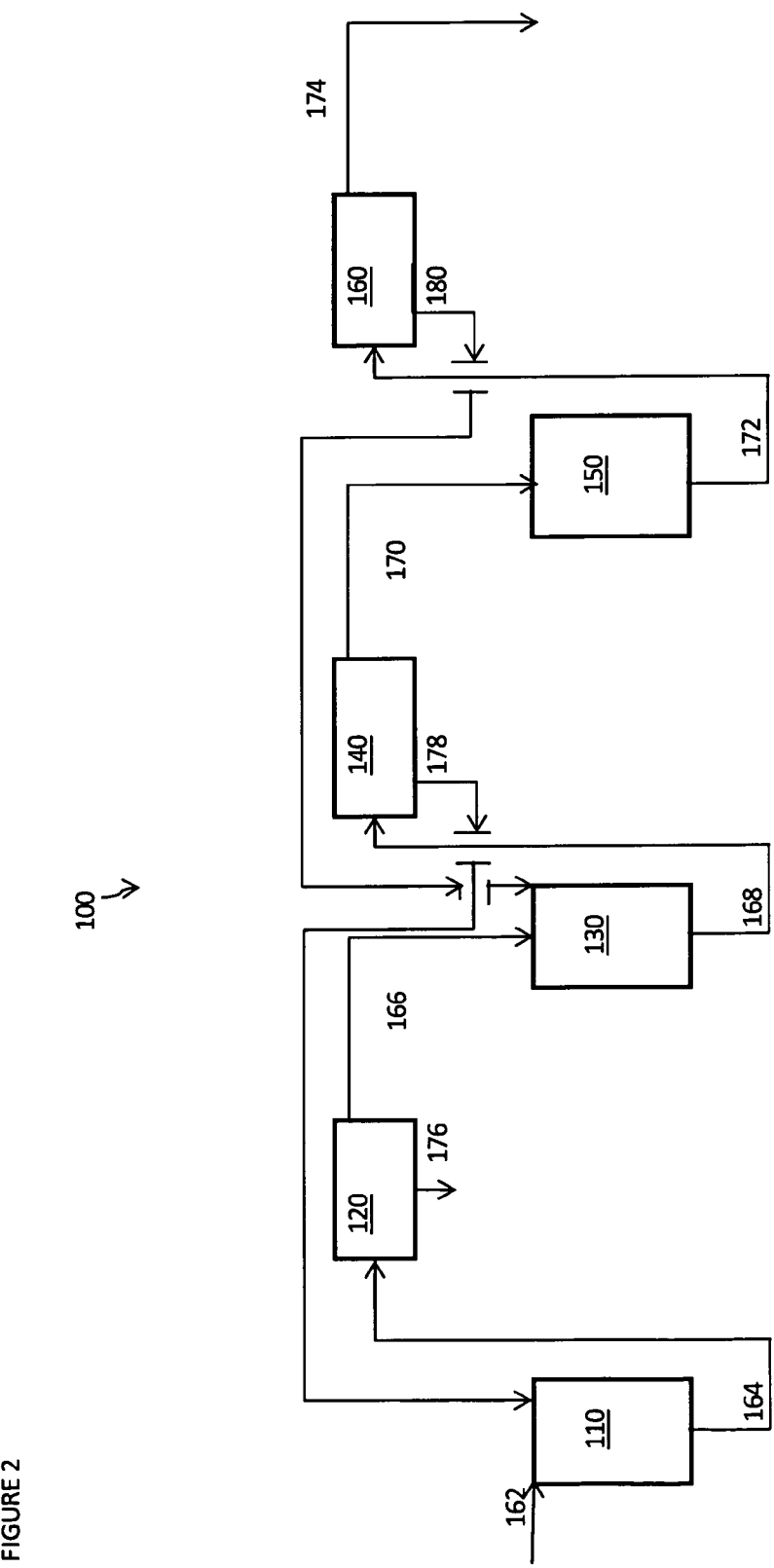
FIG. 2 is a process flow diagram illustrating an embodiment of the invention for purification of a carboxylic acid by extraction.

Water wash removes alcoholic and low boiling impurities by extraction. FIG. 2 illustrates an extraction unit 100 comprising a series of mixing vessels 110, 130, 150 and phase separation vessels, or decanters 120, 140, 160. Three extraction and phase separation steps are shown, but this number of steps is not meant to be limiting. Crude neodecanoic acid was fed via line 162 to the first mixing unit 110 and was agitated with water for 1 hour. The mixture was fed via 164 to the first decanter 120 for phase separation. Spent water was discarded via line 176. The water extraction procedure was repeated about two to three times. As shown in FIG. 2, C-10 acid was transferred from the first decanter 120 to the second mixer 130 via line 166 and subsequently to the second decanter 140 via line 168 and the third mixer 150 via line 170. The C-10 acid was transferred to the final decanter 160 via line 172 and collected from line 174 as purified C-10 acid. The water separated in decanter 160, or raffinate, via line 180, was mixed with C-10 acid in mixer 130, while the water separated in decanter 140, via line 178, was mixed with C-10 acid in mixer 110. The results are summarized in Table 8, below. Note that peroxide value is reduced to zero by this process, but the bromine value is only slightly reduced.

(3) Example 39

Hydrogenation Followed by Fractional Distillation

Alternatively, hydrogenation was applied to convert double bonds in the acid structure to single bonds and then subjected to fractional distillation with acetic anhydride to remove low boiling impurities. In this process, alcohol impurities present are made inactive by acylating them with acetic anhydride and converting them to esters, as shown in the equation below.

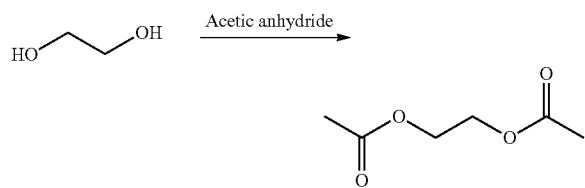

The hydrogenated C-10 acid was charged to a 10 L fractional distillation column. A vacuum of 5 mbar was applied while the temperature was gradually increased from 60 to 125° C. Volatile components were drawn off from the top of the column. The effect on the physicochemical properties of C-10 acid are apparent in Table 9, below.

(4) Example 40

Hydrogenation Followed by Flashing

In the catalytic hydrogenation process, C-10 acid is reacted in the presence of a 1% Pd/C catalyst to convert any double bonds present in the structure to single bonds, as shown, for example, in the equation below:

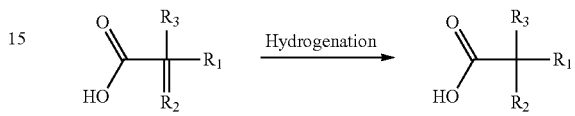

In this process, raw C-10 acid was introduced into a 5 L autoclave to which a known amount of 10% Pd/C catalyst is subsequently added. The mixture is heated for about 8 hours at about 150° C. The C-10 acid recovered from the autoclave was subsequently flashed to remove low-boiling impurities at about 125-127° C. and a vacuum of about 4 mbar in a 3 L rotary evaporator. Catalytic hydrogenation followed by flash distillation achieves dramatic improvements in the physicochemical properties of C-10 acid, as shown in Table 8, below. Note that the bromine value of the purified acid was zero, indicating that double bond components were converted to single bonds.

(5) Example 41

Hydrogenation Followed by Water Wash

Figure 3:
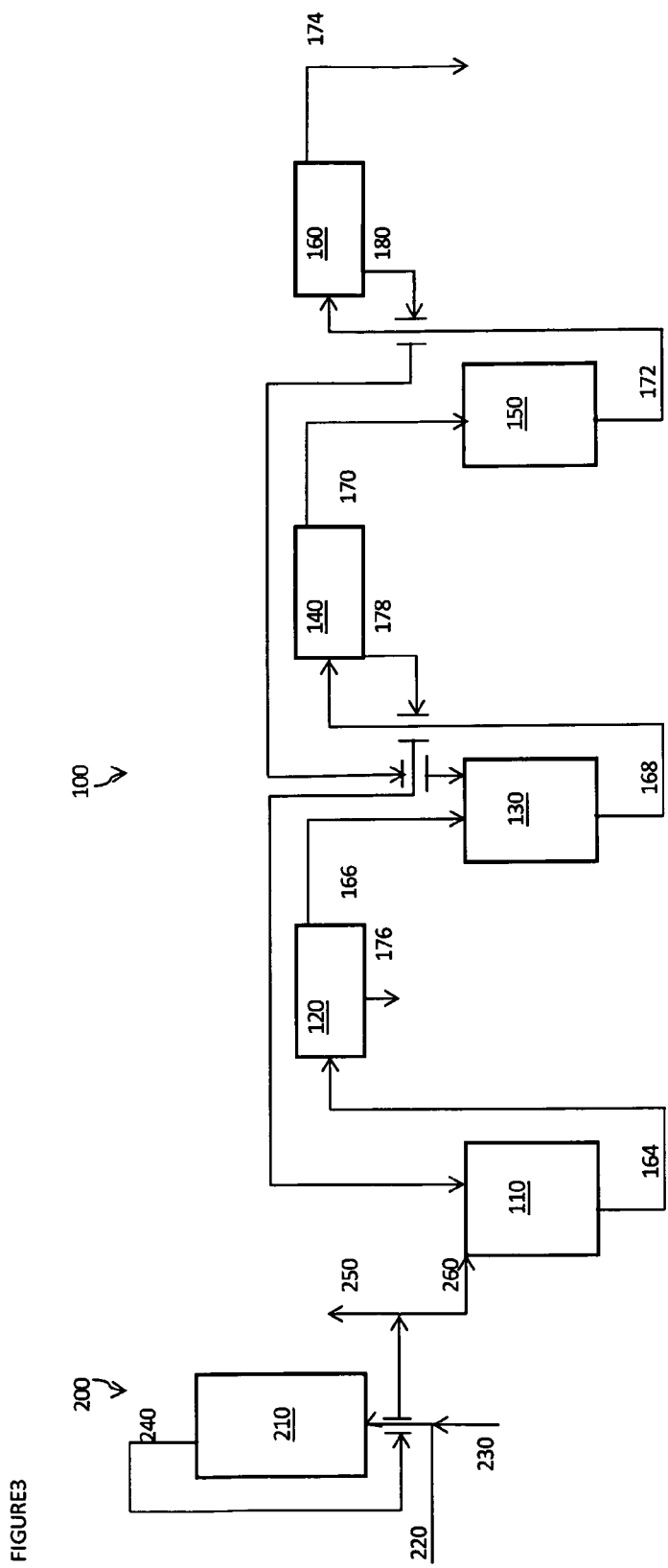
FIG. 3 is a process flow diagram illustrating another embodiment of the invention for purification of a carboxylic acid by hydrogenation followed by extraction.

In this process, structural double bonds and alcohols are removed. As shown in FIG. 3, crude C-10 acid was hydrogenated in a hydrogenation unit 200, comprising a continuous hydrogenator 210 containing a heterogeneous palladium catalyst supported on carbon, followed by extraction, as discussed with respect to Example 38, above. Crude C-10 acid was fed via line 220 with hydrogen via line 230 to the continuous hydrogenator 210. Hydrogenated neodecanoic acid with residual hydrogen was removed from the hydrogenator 210 via line 240. Residual hydrogen was vented at 250, while hydrogenated C-10 acid was sent to the extraction unit 100 via line 260. The C-10 acid was water washed as discussed in Example 38 and illustrated in FIG. 2. The results are shown in Table 8, below. Note that the bromine value and the peroxide value are both reduced to zero.

(6) Example 42

Hydrogenation Followed by Flashing and Water Wash

In this process, structural double bonds, low boiling impurities, and alcohols are removed. Crude C-10 acid was hydrogenated as discussed above. The intermediate purity acid was flashed and then agitated with water for 1 hour. The mixture was fed to a decanter for phase separation. The water extraction procedure was repeated two to three times. The results are shown in Table 8, below. Note that the bromine value and the peroxide value are both reduced to zero. Subsequent experimentation showed that the hydrogenation catalyst, Pd/C, remained active even after 50 cycles of hydrogenation.

TABLE 8

Summary of physiochemical properties of C-10 acid before and after purification

| | Example | | | | | | |
|---|---|---|---|---|---|---|---|
| | 36 | 37 | 38 | 39 | 40 | 41 | 42 |
| Properties | Crude C-10 | Flash distillation | Water wash | Hydrogenation + fractionation | Hydrogenation + flashing | Hydrogenation + water wash | Hydrogenation + flashing + water wash |
| Density (g/L) | 0.9081-0.9137 | 0.9148 | 0.9097 | 0.9075 | 0.9118-0.9124 | 0.911 | 0.9135-0.9141 |
| % Acidity (mg of KOH/g) | 326.52-358.3 | 349.56 | 318 | 336 | 302.91-310.34 | 303.7 | 318.27 |
| Bromine value (mmoles of $Br_2$/g) | 18.22-25.49 | 24.41 | 18 | 0 | 0 | 0 | 0 |
| $KMnO_4$ test | Pink color disappears | | | Pink color does not disappear | | | |
| Peroxide value (ppm) | 232.45-103384 | | 0 | | 0 | 0 | 0 |
| Water (%) | 0.00-0.97 | 0.00 | 0 | 0.07 | 0.13-0.19 | 0.12 | 0.09-0.15 |
| GC Analysis (purity, %) | 99.63-99.78 | 99.99 | 99.859 | 99.50 | 99.91-99.95 | 99.87 | 99.81-99.93 |

Performance Study of Purified C-10 Acid on Catalyst Recycle.

Trials were run using the untreated C-10 acid and the purified C-10 acid by various methods to see how purification affected catalyst recycle. The catalyst complex (diacetatopalladium (II)-2,2'-bipyridyl) for preparation of vinyl neodecanoate (NAVE-10) in reactive distillation (semi-continuous setup) was recovered with the vinyl ester product and the catalyst was recycled for ten times after recovery. Distilled vinyl acetate was provided in a molar ratio of VAM:C-10 acid of 6:1. The reaction step was operated in a 5 L autoclave for 10 hours at 100° C. The reaction mixture was cooled, weighed, and sampled for GC analysis. The vinyl ester was then recovered using a rotary evaporator. The residue was recycled for the next reaction cycle. The reaction mixture was replenished with enough C-10 acid to maintain the same amount in for each pass, and the catalyst was replenished with 10 ppm for each pass, except as noted below. The initial C-10 acid charge was 2.32 moles; make-up acid was added to maintain the mass fed to each cycle. The catalyst concentration was 1000 ppm based on the weight of carboxylic acid fed. The results are shown in Table 9, below.

TABLE 9

Effect of purification method on catalyst performance during recycle.

| | Fresh catalyst % Conversion | $1^{st}$ recycle % Conversion | $2^{nd}$ recycle % Conversion | $3^{rd}$ recycle % Conversion | $4^{th}$ recycle % Conversion | $5^{th}$ recycle % Conversion | $6^{th}$ recycle % Conversion | $7^{th}$ recycle % Conversion | $8^{th}$ recycle % Conversion | $9^{th}$ recycle % Conversion |
|---|---|---|---|---|---|---|---|---|---|---|
| Ex. 33: Untreated | 79.05 | 68.38 | 55.23 | 31.78 | 26 | — | — | — | — | — |
| Ex. 34: Flashing | 70.75 | 64.83 | 48.89 | — | — | — | — | — | — | — |
| Ex. 35: Water wash with 20 ppm catalyst added per recycle | 77.46 | 74.78 | 75.19 | 71.26 | 73.58 | 71.05 | 72.19 | 72.69 | 71.15 | 71.18 |
| Ex. 36: Hydrogenation + fractionation | 75.31 | 73.35 | 70.97 | 67.33 | 62.92 | 59.67 | — | — | — | — |
| Ex. 37: Hydrogenation + flashing | 76.97 | 73.11 | 71.40 | 68.93 | 61.77 | 58.02 | — | — | — | — |
| Ex. 37A: Hydrogenation + flashing with 50 ppm catalyst added per recycle | 74.7 | 70.94 | 71.53 | 70.41 | 66.52 | 64.11 | 46.94 | 54.23 | 44.93 | — |
| Ex. 38: Hydrogenation + water wash with 20 ppm catalyst added per recycle | 76.71 | 75.42 | 74.40 | 74.20 | 72.94 | 73.38 | 72.53 | 72.21 | 72.73 | 72.62 |
| Ex. 39: Hydrogenation + flashing + water wash with 50 ppm catalyst added per recycle | 74.34 | 75.00 | 72.89 | 70.54 | 74.00 | 67.08 | 67.82 | 65.38 | 60.51 | 62.28 |
| Ex. 39A: Hydrogenation + flashing + water wash with 20 ppm catalyst added per recycle | 74.11 | 73.82 | 73.38 | 74.05 | 71.73 | 70.85 | 70.17 | 67.67 | 68.50 | 67.33 |

As apparent in Table 9, above, water wash or water wash following hydrogenation maintained carboxylic acid conversion values surprisingly well in comparison to the other purification methods.

In light of the effects of impurities on catalyst life, a purified C-10 acid is believed essential to the successful production of NAVE-10. Properties of a pure C-10 acid are shown in Table 10, below.

TABLE 10

Preferred neodecanoic properties for use in the present invention

| Property | Value |
| --- | --- |
| Purity by GLC Method | >99.8% |
| Moisture | Nil |
| Specific gravity | 0.9135 to 0.9345 |
| Melting point | −40° C. |
| Color | <10 APHA |
| Acid value, mg KOH/gm of sample | 320 to 325 |
| Boiling point, ° C. | 262.1 |
| Vapor pressure, mm of Hg | 0.00329 @ 25° C. |
| Distillation range | 147 to 150° C./20 mm of Hg |
| Reducible substances | Nil |
| Peroxides (ppm) | Nil |
| Sulfidic impurities | Nil |
| Heavy metals | <1 ppm |

Examples 43-57

Effect of Catalyst Concentration, Temperature, and Reagent Ratio on the Conversion of Carboxylic Acids The effect of catalyst (diacetato-palladium (II)-2,2'-bipyridyl) on the conversion of 2-EHA to V-2-EH or of BA to VB was studied in a batch mode. In each case, 500 gm of 2-EHA was provided to the reactor. Vinyl acetate was provided in a molar vinyl acetate:carboxylic acid ratio of 4:1. The following tables show the effect of catalyst concentration.

TABLE 11

2-EHA Conversion as a Function of Catalyst Concentration.

| | Example No. | | | |
| --- | --- | --- | --- | --- |
| | 43 | 44 | 45 | 46 |
| Reaction volume, Liters | 1.83 | 1.83 | 1.83 | 1.83 |
| Pd concentration, ppm | 250 | 500 | 503 | 1000 |
| Maximum conversion of 2-EHA, wt % | 73.27 | 74.69 | 83.86 | 80.46 |
| Time required to attain 73% conversion, hr | 8 | 5.5 | 5.5 | 2.5 |
| Moles of product formed, gm mol | 2.54 | 2.534 | 2.534 | 2.56 |
| Product formation rate, gm mol/gm Pd per hr | 1.26 | 0.92 | 0.92 | 1.013 |
| Hourly Catalytic Productivity, kg V-2-EH/gm Pd per hr | 0.215 | 0.157 | 0.157 | 0.172 |
| Product (V-2-EH) formation rate, kg/liter reactor volume-hr | 0.03 | 0.04 | 0.04 | 0.103 |

TABLE 12

BA Conversion as a Function of Catalyst Concentration.

| | Example No. | | |
| --- | --- | --- | --- |
| | 47 | 48 | 49 |
| Reaction volume, Liters | 2.01 | 2.01 | 2.06 |
| Pd concentration, ppm | 250 | 500 | 1000 |
| Maximum conversion of BA, wt % | 78.23% | 69.88% | 74.89% |
| Time required to attain max. conversion, hr | 11.5 | 8.5 | 4.42 |
| Moles of product formed, gm mol | 3.21 | 2.86 | 3.07 |
| Product formation rate, gm mol/gm Pd per hr | 2.23 | 1.35 | 1.39 |
| Hourly Catalytic Productivity, kg VB/gm Pd per hr | 0.330 | 0.200 | 0.206 |
| Product (VB) formation rate, kg/liter reactor volume-hr | 0.02 | 0.024 | 0.05 |

For C-10 acid, the effects of catalyst concentration, reaction temperature, and molar ratio of reactants were studied. In a 5 L reactor in batch mode, neodecanoic acid was reacted with vinyl acetate in the presence of a palladium-complex catalyst. Speed of agitation was 1000 rpm. In a representative example, 400 gm of C-10 acid were reacted with vinyl acetate in a molar ratio of 3 moles vinyl acetate to one mole neodecanoic acid. The reaction took place at 90° C. in the presence of 249 mg palladium catalyst to kg of neodecanoic acid. After 11 hours, 1.10 moles of vinyl neodecanoate were formed, representing a conversion of 47.26%. The rate of formation of the product was 1.00 gm mol per gm of palladium per hour, and the productivity of the reactor was 0.20 kg of product per liter of reactor volume. Representative results are provided in Tables 13-15, below. From these tests, it was determined that an acid to vinyl acetate molar ratio of about 6 achieved optimum acid conversion, and that about 750 ppm is an optimal loading value.

TABLE 13

C-10 Acid Conversion as a Function of Catalyst Concentration.

| | Example No. | | | |
| --- | --- | --- | --- | --- |
| | 50 | 51 | 52 | 53 |
| Reaction volume, Liters | 1.10 | 1.10 | 1.10 | 1.10 |
| Pd concentration, ppm | 250 | 500 | 750 | 1000 |
| Maximum formation of NAVE-10, wt % | 55 | 97 | 90 | 86 |
| Time required to attain max. formation, hr | 11 | 11 | 11 | 11 |
| Moles of product formed, gm mol | 1.29 | 2.25 | 0.28 | 2.02 |
| Product formation rate, gm mol/gm Pd per hr | 1.18 | 1.03 | 0.63 | 0.63 |
| Hourly Catalytic Productivity, kg NAVE-10/gm Pd per hr | 0.233 | 0.203 | 0.123 | 0.125 |
| Product (NAVE-10) formation rate, kg/liter reactor volume-hr | 0.15 | 0.26 | 0.23 | 0.23 |

Temperature: 100° C.; Molar ratio of C-10 acid: VAM 1:6.

As Table 13 shows, palladium concentrations of greater than 250 ppm are preferable to achieve satisfactory formation of vinyl neodecanoate. Further analysis has shown that at concentrations from 250 to 750 ppm, equilibrium conversion was not achieved. Therefore, concentrations of greater than 750 ppm are preferable.

TABLE 14

C-10 Acid Conversion as a Function of Temperature.

| | Example No. | | |
|---|---|---|---|
| | 54 | 53 | 55 |
| Reaction volume, Liters | 1.10 | 1.10 | 1.10 |
| Temperature, ° C. | 90 | 100 | 110 |
| Maximum formation of NAVE-10, wt % | 80 | 87 | 92 |
| Time required to attain max. formation, hr | 10 | 6 | 5 |
| Moles of product formed, gm mol | 1.84 | 2.02 | 2.14 |
| Product formation rate, gm mol/gm Pd per hr | 0.42 | 0.63 | 1.08 |
| Hourly Catalytic Productivity, kg NAVE-10/gm Pd per hr | 0.084 | 0.125 | 0.215 |
| Product (NAVE-10) formation rate, kg/liter reactor volume-hr | 0.21 | 0.23 | 0.24 |

Catalyst loading: 1000 ppm; molar ratio of C-10 acid: VAM 1:6.

As Table 14 shows, as the temperature increases, the rate of formation of vinyl neodecanoate increases.

TABLE 15

C-10 Acid Conversion as a Function of VAM to C-10 Acid Molar Ratio.

| | Example No. | | |
|---|---|---|---|
| | 56 | 53 | 57 |
| Reaction volume, Liters | 1.10 | 1.10 | 1.10 |
| Molar Ratio, VAM to C-10 acid | 3:1 | 6:1 | 9:1 |
| Maximum formation of NAVE-10, wt % | 86 | 86 | 97 |
| Time required to attain max. formation, hr | 8 | 6 | 9 |
| Moles of product formed, gm mol | 2.13 | 2.02 | 2.15 |
| Product formation rate, gm mol/gm Pd per hr | 0.49 | 0.63 | 0.63 |
| Hourly Catalytic Productivity, kg NAVE-10/gm Pd per hr | 0.097 | 0.125 | 0.125 |
| Product (NAVE-10) formation rate, kg/liter reactor volume-hr | 0.38 | 0.23 | 0.18 |

Catalyst loading: 1000 ppm; Temperature: 100° C.

Examples 58-66

Pilot Scale Study of Additional Carboxylic Acids

Example 58

Following the procedure of Example 1, methacrylic acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of methacrylic acid to vinyl methacrylate is achieved.

Example 59: Following the procedure of Example 1 or 2, propionic acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of propionic acid to vinyl propionate is achieved.

Example 60: Following the procedure of Example 1 or 2, butyric acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of butyric acid to vinyl butyrate is achieved.

Example 61: Following the procedure of Example 1 or 2, valeric acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of valeric acid to vinyl valerate is achieved.

Example 62: Following the procedure of Example 1, heptanoic acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of heptanoic acid to vinyl heptanoate is achieved.

Examples 63-64: Following the procedure of Example 1 or 2, neodecanoic acid, a mixture of neoalkanoic acids having on average ten carbon atoms, was reacted with vinyl acetate in a molar ratio of from about 2 moles of vinyl acetate per mole of carboxylic acid in the presence of a palladium catalyst in a concentration of from about 500 to about 1000 ppm based on the mass of carboxylic acid. The reaction mixture is maintained at about 99 to 102° C. until the desired conversion of neodecanoic acid to the corresponding vinyl ester, vinyl neodecanoate (also referred to herein as neo-acid vinyl ester-10 or NAVE-10), is achieved. Samples were periodically drawn from the reaction mixture and analyzed via high-performance liquid chromatography (HPLC).

Initial recovery of vinyl acetate and acetic acid was completed at about 60° C. with a vacuum of about 5 mbar. The temperature was then gradually increased to about 95° C. Vinyl neodecanoate was allowed to distill and was separately collected. NAVE-10 starts to distill at 90° C. The distillate mainly contained NAVE-10 and a small amount of acetic acid and vinyl acetate, and is herein identified as crude NAVE-10. The residue contained mainly neodecanoic acid, a small amount of vinyl decanoate, and the catalyst. The results are provided in Table 16, and an analysis of the product is provided in Table 17, below.

TABLE 16

Vinyl ester production reaction performance.

| | Example 63: Vinyl neodecanoate production: Fresh catalyst @ 750 ppm | Example 64: Vinyl neodecanoate production: Fresh catalyst @ 1000 ppm |
|---|---|---|
| Size of pilot batch, L | 3.5 | 3.5 |
| Formation of NAVE-10 ester, wt % (based on weight of reaction mixture in reactor and reboiler), fresh catalyst | 80.86 | 90.90 |
| Formation of NAVE-10 ester, wt %, 1$^{st}$ recycle | 75.44 | 77 |
| Moles of carboxylic acid input | 11.63 | 11.63 |
| Amount of product formed, gm mol | 9.4 | 10.53 |
| Reaction time (Initial charge heating + Feeding mixture + Time required to achieve conversion), hr | 8 | 8 |
| VAM recycle rate to transvinylation reactor, L/h | 1.2 | 1.5 |
| Average product formation rate, gm mol of vinyl ester/1 gm of Palladium-per hr | 1.55 | 1.32 |

TABLE 16-continued

Vinyl ester production reaction performance.

| | Example 63: Vinyl neodecanoate production: Fresh catalyst @ 750 ppm | Example 64: Vinyl neodecanoate production: Fresh catalyst @ 1000 ppm |
|---|---|---|
| Turn Over Number (TON) of catalyst at the end of one fresh & two recycle runs, kg of vinyl ester/1 gm of Palladium | 5.615 | 3.865 |
| Hourly Catalytic Productivity, kg vinyl ester/gm Palladium/hr | 0.310 | 0.262 |
| Rate of formation of product, kg/l-h | 0.066 | 0.074 |
| Productivity of vinyl ester, kg of vinyl ester/Liter | 0.519 | 0.59 |

Note:
The catalyst was active after recycle.

Another reaction was performed in a thermosiphon reactor. The reactor was fed VAM and C-10 acid at a molar ratio of about 2 moles of VAM per mole of C-10 acid and catalyst at a concentration of 1000 ppm Pd based on the amount of C-10 acid. The reaction system was operated in the same manner as described above. The reactor temperature reached about 98° C. and was operated for about 10 hours. At the end of this period, the reactor contents were analyzed and found to contain 57.52% vinyl neodecanoate, 22.66% vinyl acetate, 16.42% neodecanoic acid, and 3.40% acetic acid, achieving 77.79% formation of NAVE-10. Characteristics of the NAVE-10 product are presented in Table 17, below.

TABLE 17

Analysis of Vinyl Ester Product from Pilot Plant Runs.

| | Examples 63-64 |
|---|---|
| Analytical parameter | Observed value |
| Density | 0.8770 gm/cc @ 25° C. |
| Acid value | 0.153 mg of KOH/gm of sample |
| Purity by GC | 99.7% |
| APHA Value | 6.81 |
| MS Spectra | COMPLIES |
| NMR | COMPLIES |

Example 65: Following the procedure of Example 1 or 2, acrylic acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of acrylic acid to vinyl acrylate is achieved.

Example 66: Following the procedure of Example 1 or 2, stearic acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of stearic acid to vinyl stearate is achieved.

Example 67: Following the procedure of Example 1, palmitic acid is reacted with vinyl acetate in a molar ratio of from about 1.5 to about 3 moles of vinyl acetate per mole of carboxylic acid in the presence of a palladium catalyst in a concentration of from about 100 to about 200 ppm based on the mass of carboxylic acid. The reaction mixture is maintained at about 100° C. until the desired conversion of palmitic acid to vinyl palmitate is achieved.

There is thus provided in accordance with the present invention a semi-continuous process for selective formation of a vinyl ester from its corresponding carboxylic acid. In the formation process, a carboxylic acid, such as benzoic acid or 2-ethylhexanoic acid, and vinyl acetate are fed to a reactor and reacted in the presence of a homogeneous transvinylation catalyst in a reaction mixture to form a vinyl ester product, such as vinyl benzoate or vinyl 2-ethylhexanoate, and acetic acid. Acetic acid and vinyl acetate are preferably continuously removed from the reaction mixture and at least a portion of the vinyl acetate is separated from the acetic acid and recycled to the reaction mixture. The reaction mixture may be periodically withdrawn as a crude vinyl ester product mixture and a purified vinyl ester product may be separated from residual carboxylic acid, residual vinyl acetate, residual acetic acid, and homogeneous transvinylation catalyst.

The process according to the invention is generally characterized by a conversion of carboxylic acid to vinyl ester product with a selectivity of at least 80 mole %, and a crude product mixture containing less than 15 weight % acetic acid. These characteristics may be achieved by selection of catalyst and by controlling the reaction conditions, feed to the reaction mixture, removal of acetic acid from the reaction mixture, and the separation and recycling of vinyl acetate to the reaction mixture. A molar ratio of vinyl acetate:carboxylic acid of from 1:1 to 4:1 is typically maintained in the reaction mixture.

Preferably, the process is characterized by an Hourly Catalytic Productivity of at least 0.05 kg vinyl product per gm catalyst metal per hour. More preferably, the process is characterized by an Hourly Catalytic Productivity of at least 0.1 kg vinyl product per gm catalyst metal per hour. Still more preferably, the process is characterized by an Hourly Catalytic Productivity of from about 0.1 to about 0.4 kg vinyl product per gm catalyst metal per hour. In one embodiment, there is less than 10 weight % acetic acid in the crude product mixture as well as a molar ratio of vinyl acetate:carboxylic acid of from 1:1 to 4:1 generally maintained in the reaction mixture. In another embodiment, the acetic acid concentration in the crude product mixture is less than 5 weight % at the vinyl acetate:carboxylic acid molar ratio of from 1:1 to 4:1. In still another embodiment, the acetic acid concentration in the crude product mixture is less than 15 weight % at a vinyl acetate:carboxylic acid molar ratio of from about 1.5:1 up to about 3:1 in the reaction mixture. In yet another embodiment, the acetic acid concentration in the crude product mixture is less than 15 weight % acetic acid in with a vinyl acetate:carboxylic acid molar ratio of more than 2:1 in the reaction mixture.

The process generally comprises accumulating crude vinyl ester product in the reaction mixture and periodically recovering product therefrom. Preferably, the reaction time is from about 15 minutes or about 1 hour to about 40 hours; more preferably, from about 2 hours to about 20 hours; and still more preferably, from about 3 hours to about 15 hours.

Generally, the process comprises separating residual carboxylic acid from the crude vinyl ester product mixture and recycling the residual carboxylic acid to the reaction mixture. Typically, the process further comprises separating the homogeneous transvinylation catalyst from the crude vinyl ester product mixture and recycling the catalyst to the reaction mixture. Preferably, the separated vinyl acetate is recycled at a rate of less than 8 kg of vinyl acetate for every kg of vinyl ester produced. More preferably, the vinyl acetate is recycled at a rate of less than 7 kg per kg of vinyl product. Still more preferably, the vinyl acetate is recycled at a rate of less than 6 kg of vinyl acetate per kg of vinyl product.

The inhibitor is generally selected from the group consisting of hydroquinone (HQ), methoxy hydroquinone (MEHQ), butylated hydroxytoluene (BHT), tert-butyl catechol (TBC), diphenylamine, phenothiazine and a hindered phenol. The carboxylic acid is generally selected from the group consisting of 2-ethylhexanoic acid, benzoic acid, methacrylic acid, neodecanoic acid, propionic acid, butyric acid, valeric acid, heptanoic acid, acrylic acid, stearic acid, and palmitic acid.

In one embodiment, more than 70 weight % of the carboxylic acid provided is converted to vinyl ester. The carboxylic acid conversion recited may likewise refer to ester conversion as defined herein. The process is generally characterized by a selectivity of greater than 90 mole %, typically greater than 95 mole %, in one aspect of the invention, based on the carboxylic acid provided. Preferably, the process is characterized by a selectivity of greater than 99 mole %. In accordance with the invention, the reaction is carried out under reactive distillation conditions wherein vinyl acetate and by-product acetic acid are removed as distillate from the reaction mixture. The temperature of the reaction is generally maintained at from about 80° C. up to about 120° C. Preferably, the temperature is from about 90° C. to about 110° C. More preferably, the temperature is from about 90° C. to about 105° C.

Typically, unreacted vinyl acetate and acetic acid are continuously removed from the reaction mixture in a vinyl acetate:acetic acid molar ratio of from about 5:1 to about 25:1, and in some cases, in a vinyl acetate:acetic acid molar ratio of from about 6:1 to about 10:1.

Preferably, the homogeneous transvinylation catalyst comprises a platinum group metal.

A particularly useful commercial embodiment is a semi-continuous process for selective formation of vinyl ester by reactive distillation from its corresponding carboxylic acid. Carboxylic acid and vinyl acetate are reacted in the presence of a palladium acetate—bidentate ligand catalyst complex in a reaction mixture to form a vinyl ester product and acetic acid while the acetic acid and vinyl acetate are continuously removed from the reaction mixture. At least a portion of the removed vinyl acetate is separated from the removed acetic acid and recycled to the reaction mixture. The reaction mixture is periodically withdrawn as a crude vinyl ester product mixture which includes residual carboxylic acid, residual vinyl acetate, residual acetic acid, and palladium acetate—bidentate ligand catalyst complex. Residual reactants including carboxylic acid and vinyl acetate; residual acetic acid byproduct; and catalyst complex are separated from the crude vinyl ester product mixture to form a purified vinyl ester product.

The process is characterized by a vinyl product selectivity of at least 80 mole % and an acetic acid concentration present in the crude product mixture of less than 15 weight %. These characteristics are achieved by catalyst selection and control of the reaction conditions, feed to the reaction mixture, removal of acetic acid from the reaction mixture, and the separation and recycling of vinyl acetate to the reaction mixture.

In accordance with the present invention, a molar ratio of vinyl acetate:carboxylic acid of from 1:1 to 10:1 or 1:1 to 4:1 is generally maintained in the reaction mixture. The catalyst concentration provided is generally from about 50 or 150 parts palladium per million to about 2325 or about 3000 parts palladium per million parts of carboxylic acid provided. Preferably, the catalyst concentration is from about 500 to about 1500 parts palladium per million parts of carboxylic acid.

Typically, the process comprises accumulating crude vinyl ester product in the reaction mixture and periodically recovering product therefrom.

Generally, the process is characterized by an initial turnover number of more than about 3 kg of vinyl ester per gram of palladium contained in the palladium acetate—bidentate ligand catalyst complex utilized. In one embodiment, the initial turnover number is more than about 15 kg of vinyl ester per gram of palladium. In another embodiment, the initial turnover number is more than 20 kg of vinyl ester per gram of palladium.

The catalyst complex is characterized by a mole ratio of palladium acetate to bidentate ligand of from about 1:1 to about 1:1.5 or about 1:2. The bidentate ligand is selected from the group consisting of 2,2'-bipyridyl, 1,10-phenanthroline, N,N,N',N'-tetramethylethylenediamine and P,P,P',P'-tetraphenyl-1,2-diphosphinoethane.

In an aspect of the invention, the carboxylic acid may be purified prior to reaction. A purified carboxylic acid is generally evidenced by a bromine value of less than 20 mmoles of $Br_2$/g, a peroxide value of less than 200 ppm, or a permanganate time of at least 30 minutes.

One embodiment provides for a semi-continuous process for selective formation of vinyl ester from neodecanoic acid. Raw neodecanoic acid is purified and then reacted with vinyl acetate in the presence of a homogeneous transvinylation catalyst to form a vinyl neodecanoate product and acetic acid. Acetic acid and vinyl acetate are preferably continuously removed from the reaction mixture and at least a portion of the vinyl acetate is separated from the acetic acid and recycled to the reaction mixture. The reaction mixture may be periodically withdrawn and vinyl neodecanoate product may be separated from residual neodecanoic acid, residual vinyl acetate, residual acetic acid, and homogeneous transvinylation catalyst. The process is generally characterized by a conversion of neodecanoic acid to vinyl ester product with a selectivity of at least 80 mole %, and a crude product mixture containing less than 15 weight % acetic acid.

More specifically, one embodiment provides for a process for purifying a carboxylic acid. In this embodiment, a raw carboxylic acid is purified using a method selected from the group consisting of flash distillation; fractionation; extraction; hydrogenation; and combinations thereof. The purification process is characterized by a purified carboxylic acid containing less than 1 weight % impurities selected from the group consisting of compounds having alcohol functional groups; compounds having ester functional groups; compounds having olefinic functional groups; compounds having peroxide functional groups; sulfur; and other electropositive metals.

The purification method may include at least hydrogenation. The hydrogenation may be performed with a palladium catalyst supported on carbon or another suitable catalyst that remains active for several cycles of hydrogenation; such as for at least about 25 cycles and up to about 50 cycles of hydrogenation or for at least 50 cycles of hydrogenation; in any case, the catalyst preferably remains active for more than about 30 cycles of hydrogenation. The conditions may include a temperature in the range of about 50-150° C. temperature and a temperature in the range of about 5-25 kg/cm² pressure.

Alternatively, the purification method may include at least multistage extraction with water. In the extraction step, the carboxylic acid is agitated with water for from about ½ hour to about 6 hours, such as for about 2 hours. The carboxylic acid is subsequently recovered by phase separation, for which the carboxylic acid-water mixture is allowed to settle for from about 10 minutes to about 2 hours.

While the invention has been described in detail, modifications within the spirit and scope of the invention will be readily apparent to those of skill in the art. In view of the foregoing discussion, relevant knowledge in the art and references including co-pending applications discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A semi-continuous process for selective formation of vinyl ester from its corresponding carboxylic acid, the process comprising:
    (a) providing a carboxylic acid, vinyl acetate, and a homogeneous transvinylation catalyst comprising palladium to a reaction mixture;
    (b) reacting the carboxylic acid and vinyl acetate in the presence of the homogeneous transvinylation catalyst comprising palladium in the reaction mixture to form a vinyl ester product and acetic acid;
    (c) continuously removing acetic acid and vinyl acetate from the reaction mixture in a molar ratio of vinyl acetate:acetic acid of 0.5:1 to 14.4:1;
    (d) separating at least a portion of the removed vinyl acetate from the removed acetic acid and recycling the separated vinyl acetate to the reaction mixture;
    (e) withdrawing reaction mixture as a crude vinyl ester product mixture which includes residual carboxylic acid, residual vinyl acetate, residual acetic acid, and homogeneous transvinylation catalyst; and
    (f) separating residual carboxylic acid, residual vinyl acetate, residual acetic acid, and homogeneous transvinylation catalyst from the crude vinyl ester product mixture to form a purified vinyl ester product;
wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture.

2. The process according to claim 1, wherein the reaction conditions, feed to the reaction mixture, removal of acetic acid from the reaction mixture, and the separation and recycling of vinyl acetate to the reaction mixture are controlled and the catalyst is selected such that a molar ratio of vinyl acetate:carboxylic acid of from 1:1 to 9:1 is maintained in the reaction mixture.

3. The process according to claim 1, wherein the reaction conditions, feed to the reaction mixture, removal of acetic acid from the reaction mixture, and the separation and recycling of vinyl acetate to the reaction mixture are controlled and the catalyst is selected such that the process is characterized by an Hourly Catalytic Productivity of at least 0.05 kg vinyl product per gm catalyst metal per hour.

4. The process according to claim 1, wherein the reaction conditions, feed to the reaction mixture, removal of acetic acid from the reaction mixture, and the separation and recycling of vinyl acetate to the reaction mixture are controlled and the catalyst is selected such that the process is characterized by an Hourly Catalytic Productivity of at least 0.1 kg vinyl product per gm catalyst metal per hour.

5. The process according to claim 1, wherein the reaction conditions, feed to the reaction mixture, removal of acetic acid from the reaction mixture, and the separation and recycling of vinyl acetate to the reaction mixture are controlled and the catalyst is selected such that the process is characterized by an Hourly Catalytic Productivity of from about 0.1 to about 0.4 kg vinyl product per gm catalyst metal per hour.

6. The process according to claim 1, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 10 weight % acetic acid in the crude product mixture as well as a molar ratio of vinyl acetate: carboxylic acid of from 1:1 to 9:1 maintained in the reaction mixture.

7. The process according to claim 1, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 5 weight % acetic acid in the crude product mixture as well as a molar ratio of vinyl acetate: carboxylic acid of from 1:1 to 9:1 maintained in the reaction mixture.

8. The process according to claim 1, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate: carboxylic acid of from about 1.5:1 up to about 4:1 maintained in the reaction mixture.

9. The process according to claim 7, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate: carboxylic acid of more than 2:1 is maintained in the reaction mixture.

10. The process according to claim 1, wherein the reaction time for the process is from about 2 hours to about 20 hours.

11. The process according to claim 1, wherein the separated vinyl acetate is recycled at a rate of less than 8 kg of vinyl acetate for every kg of vinyl ester produced.

12. The process according to claim 1, wherein the carboxylic acid is selected from the group consisting of 2-ethylhexanoic acid, benzoic acid, neodecanoic acid, propionic acid, butyric acid, valeric acid, heptanoic acid, acrylic acid, methacrylic acid, stearic acid, and palmitic acid.

13. A semi-continuous process for selective formation of vinyl ester by reactive distillation from its corresponding carboxylic acid, the process comprising:
    (a) providing carboxylic acid, vinyl acetate, and a palladium acetate—bidentate ligand catalyst complex to a reaction mixture;
    (b) reacting the carboxylic acid and vinyl acetate in the presence of the palladium acetate—bidentate ligand catalyst complex in the reaction mixture to form a vinyl ester product and acetic acid;

(c) continuously removing acetic acid and vinyl acetate from the reaction mixture;

(d) separating at least a portion of the removed vinyl acetate from the removed acetic acid and recycling the separated vinyl acetate to the reaction mixture;

(e) withdrawing reaction mixture as a crude vinyl ester product mixture which includes residual carboxylic acid, residual vinyl acetate, residual acetic acid, and palladium acetate—bidentate ligand catalyst complex; and (f) separating residual carboxylic acid, residual vinyl acetate, residual acetic acid, and palladium acetate—bidentate ligand catalyst complex from the crude vinyl ester product mixture to form a purified vinyl ester product;

wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture;

and wherein further a molar ratio of vinyl acetate:carboxylic acid of from about 2:1 up to about 9:1 is maintained in the reaction mixture.

14. A semi-continuous process for selective formation of vinyl ester from neodecanoic acid, the process comprising:

(a) purifying raw neodecanoic acid such that the purified neodecanoic acid is characterized by at least one of:
  i) a bromine value of less than 20 mmoles of $Br_2/g$;
  (ii) a peroxide value of less than 200 ppm; or
  (iii) permanganate time of at least 30 minutes;

(b) reacting the purified neodecanoic acid and vinyl acetate in the presence of a homogeneous transvinylation catalyst comprising palladium in a reaction mixture to form a vinyl ester product and acetic acid;

(c) continuously removing acetic acid and vinyl acetate from the reaction mixture and recycling at least a portion of the vinyl acetate to the reaction mixture;

(d) withdrawing the reaction mixture and separating vinyl neodecanoate product from the reaction mixture;

wherein the reaction conditions, feed to the reaction mixture, removal of acetic acid from the reaction mixture, and recycling of vinyl acetate to the reaction mixture are controlled and the catalyst is selected such that neodecanoic acid is converted to vinyl ester product with a selectivity of at least 80 mole %, and there is less than 15 weight % acetic acid in the crude product mixture.

* * * * *